United States Patent
Blake et al.

(10) Patent No.: US 10,653,822 B2
(45) Date of Patent: *May 19, 2020

(54) DRUG DELIVERY DEVICES AND METHODS OF MAKING AND USING SAME

(71) Applicant: The Administrators of the Tulane Educational Fund, New Orleans, LA (US)

(72) Inventors: Diane A. Blake, Mandeville, LA (US); Vijay T. John, Destrahan, LA (US); Ramesh Ayyala, New Orleans, LA (US); Thiruselvam Ponnusamy, Beaverton, OR (US)

(73) Assignee: THE ADMINSTRATORS OF THE TULANE EDUCATIONAL FUND, New Orleans, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/101,413

(22) Filed: Aug. 11, 2018

(65) Prior Publication Data
US 2018/0344905 A1    Dec. 6, 2018

Related U.S. Application Data

(63) Continuation of application No. 14/633,282, filed on Feb. 27, 2015, now Pat. No. 10,058,640, which is a continuation of application No. PCT/US2013/057336, filed on Aug. 29, 2013.

(60) Provisional application No. 61/694,455, filed on Aug. 29, 2012.

(51) Int. Cl.
| | |
|---|---|
| A61L 31/16 | (2006.01) |
| A61K 9/70 | (2006.01) |
| A61L 31/10 | (2006.01) |
| A61L 31/14 | (2006.01) |
| A61K 31/216 | (2006.01) |
| A61K 31/407 | (2006.01) |
| A61K 31/513 | (2006.01) |
| A61K 47/34 | (2017.01) |
| B29C 39/00 | (2006.01) |
| B29C 39/08 | (2006.01) |
| B29C 39/12 | (2006.01) |
| B29D 7/01 | (2006.01) |
| A61M 37/00 | (2006.01) |
| A61F 9/007 | (2006.01) |
| B29K 33/00 | (2006.01) |

(52) U.S. Cl.
CPC ............ *A61L 31/16* (2013.01); *A61K 9/7007* (2013.01); *A61K 31/216* (2013.01); *A61K 31/407* (2013.01); *A61K 31/513* (2013.01); *A61K 47/34* (2013.01); *A61L 31/10* (2013.01); *A61L 31/146* (2013.01); *A61L 31/148* (2013.01); *B29C 39/003* (2013.01); *B29C 39/08* (2013.01); *B29C 39/123* (2013.01); *B29D 7/01* (2013.01); *A61F 9/00781* (2013.01); *A61L 2300/414* (2013.01); *A61L 2300/434* (2013.01); *A61L 2300/45* (2013.01); *A61L 2420/06* (2013.01); *A61L 2420/08* (2013.01); *A61M 37/00* (2013.01); *B29K 2033/00* (2013.01); *B29K 2995/006* (2013.01); *B29K 2995/0056* (2013.01)

(58) Field of Classification Search
None
See application file for complete search history.

(56) References Cited

U.S. PATENT DOCUMENTS

2006/0269475 A1* 11/2006 Ryu ..................... A61K 9/0097
424/1.11

OTHER PUBLICATIONS

Ponnusamy et al., In vitro degradation and release characteristics of spin coated thin films of PLGA with a "breath figure" morphology, Biomatter 2:2, 77-86; Apr. 2012 (Year: 2012).*

* cited by examiner

*Primary Examiner* — Jennifer A Berrios
(74) *Attorney, Agent, or Firm* — Edna Vassilovski

(57) ABSTRACT

The disclosure provides drug delivery devices and methods of making and using the drug delivery devices. The devices include single and multi-layer polymer films made by a breath figure technique having therapeutic agents associated therewith. For example, the devices may be a dual layer polymer film wherein the first layer includes a therapeutic agent incorporated into it by spin coating the first agent with a polymer solution and the second agent is incorporated into the second layer by loading the agent into pores of the second layer after it is spin coated onto the first layer. In some cases one layer provides a burst release and the second layer provides a slow release drug delivery profile. The devices may take on the form of a surgical mesh with a slow release therapeutic drug.

15 Claims, 31 Drawing Sheets

Day 7

Day 14

Day 21

Day 28

Day 35

Day 7

Day 14

Day 21

Day 28

Day 35

Day 7

Day 14

Day 21

Day 35

Day 7

Day 14

Day 21

Day 35

Figure 24
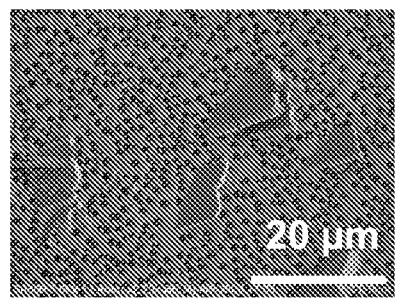
Figure 25
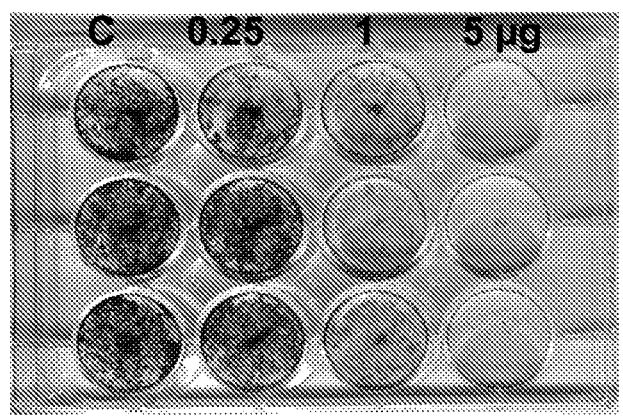
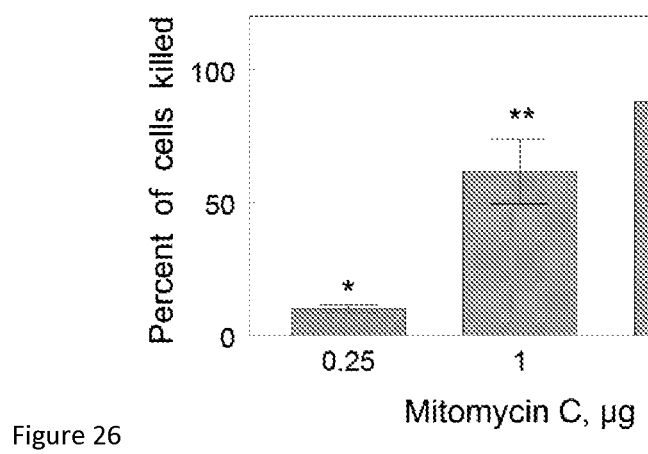
Figure 26

Day 7

Day 14

Day 28

DRUG DELIVERY DEVICES AND METHODS OF MAKING AND USING SAME

CROSS-REFERENCE TO RELATED APPLICATIONS

This application is a continuation of U.S. patent application Ser. No. 14/633,282, filed on Feb. 27, 2015, entitled "DRUG DELIVERY DEVICES AND METHODS OF MAKING AND USING SAME," which is a continuation of International Application No. PCT/US2013/057336, entitled "DRUG DELIVERY DEVICES AND METHODS OF MAKING AND USING SAME," filed on Aug. 29, 2013, which claims the benefit of priority to U.S. Provisional Patent Application No. 61/694,455, entitled, "BIOLOGICAL SURGICAL FILMS FOR THE TREATMENT OF GLAUCOMA AND METHODS FOR PRODUCING THE SAME," filed Aug. 29, 2012. The aforementioned US Patent Application, PCT application and US Provisional application are herein incorporated by reference in their entirety. U.S. patent application Ser. No. 12/277,139, U.S. Provisional Patent Application No. 61/516,580, and U.S. Provisional Patent Application No. 61/516,689 are also hereby incorporated by reference in their entirety.

FIELD OF THE INVENTION

The disclosure relates to devices for drug delivery, methods of making the devices, and methods of using the devices for drug delivery. The disclosure also relates to therapeutic films and devices comprising the therapeutic films for drug delivery, methods of making the therapeutic films and devices comprising the therapeutic films, and methods of using the therapeutic films and devices comprising the therapeutic films for drug delivery.

BACKGROUND

Poly (lactic-co-glycolic acid) (PLGA), a biodegradable and biocompatible FDA approved polymer, is being increasingly used in sustained drug delivery applications. Some biodegradable materials have been designed for glaucoma, however, these are generally implants that must reside in the eye and are limited in their delivery. Glaucoma drainage devices, for example, have been used for some time to release intraocular pressure by allowing flow of the aqueous humor from the anterior chamber of the eye. Some of these devices have been situated with therapeutics that can be released over time. However many of these formulations struggle with appropriate release profiles.

Reduction and control of the intraocular pressure (IOP) is the mainstay of treatment in the management of glaucoma. Elevated IOP can be reduced pharmacologically via daily eyedrops, or surgically by trabeculectomy and/or implantation of a glaucoma drainage device (GDD). What currently limits enthusiasm for GDDs is the development of inner wall bleb fibrosis, which hampers outflow facility and increases intraocular pressure. The success rate of GDD implants is ~70% to 80% at one year and 40% to 50% five years postoperatively because of the development of fibrosis. A GDD that could regulate flow without the development of fibrosis could potentially become a first line treatment for glaucoma.

Invasiveness and metastatic dissemination characterize neuroectodermal tumors such as glioblastoma, neuroblastoma, medulloblastoma and melanoma. Despite the growing knowledge about their etiology and efforts to develop improved tools for early diagnosis and treatment, their invasive phenotype causes high mortality rate, especially among children and young adults. Brain tumors are particularly difficult to treat due to distinct anatomical and physiological traits of neural tissue and vasculature. The blood brain barrier (BBB) and blood-brain tumor barrier (BTB) represent the major obstacles that prevent chemotherapeutic agents from reaching intracranial tumors.

Several strategies have been developed to enhance the BBB and BTB permeability via biochemical intervention. Carotid artery infusion with hyperosmotic (1.6 M) mannitol was shown to temporarily open BBB, by induction of endothelial cells shrinkage and tight junction disruption. However, the opening lasts less than 30 minutes, leaving a very narrow window for potential drug delivery. Another strategy for more selective BTB opening involves the use of vasomodulators, mostly bradykinin or nitric oxide donors, which are able to transiently (for 15-120 minutes) increase capillary permeability. The main caveat associated with the use of bradykinin involves its ability to promote glioma cell migration, invasion and tumor angiogenesis and to act as a chemoattractant guiding glioma cells to the blood vessels. These effects increase aggressiveness of the tumor. For that reason, bradykinin B2 receptor antagonists have been proposed to be candidate anti-invasive drugs.

A number of unanswered questions remain about how to facilitate chemotherapeutic drug penetration and access to brain tumor tissue, and about how to develop new, more effective multidrug targeted regimens against glial tumors.

SUMMARY

This disclosure provides devices for drug delivery, methods of making the devices, and methods of using the devices for drug delivery. In some embodiments, the devices are therapeutic films including devices comprising the therapeutic films (such as devices coated with the therapeutic films or devices which are otherwise associated with or attached to the therapeutic films). In some embodiments, the devices are surgical devices which are configured for implantation in a patient, for example the devices are made from biocompatible materials and in further embodiments may be biodegradable. In some embodiments, the therapeutic films are single or multi-layer films comprising one or more therapeutics. In further embodiments, the therapeutic films are multi-layered films designed to provide a burst release of a therapeutic, a sustained release of a therapeutic or both. In further embodiments, the therapeutic films are multi-layered films wherein one layer provides a burst release of a therapeutic agent and a second layer provides a sustained release of a therapeutic agent. In some embodiments the methods are methods of making devices which comprise forming layers of polymeric film using a breath figure technique. In some embodiments, the methods involve using the devices for treating a patient in need thereof, for example implanting a device in the body of a patient at a site in need of treatment. For example, the devices can be used for glaucoma therapy and can be implanted in a subconjunctival space for release of therapeutics. As another example, the devices can be implanted at the site of a tumor for release of therapeutics to shrink or treat the tumor.

In some embodiments, the present disclosure provides a film with a therapeutic agent that may be attached to a glaucoma drainage device ("GDD") that may be implanted into an animal. An example of a suitable GDD is an Ahmed valve. However, other GDDs may also be used such as any GDD including a plate and a tube, including the Baerveldt tube shunt. The film may comprise a dual layer breath-figure PLGA film where one layer provides an immediate release, while a second layer provides a slower release. In some embodiments, the film may allow for the release of the therapeutic agent over time. The film is useful for the treatment of glaucoma (for example, the fibrosis that accompanies the implantation of a glaucoma drainage device) and other indications that require a time-release therapeutic.

The present disclosure also provides methods to fabricate a thin drug-containing polymer coating for medical devices. In some embodiments, the present disclosure provides a simple and scalable method to fabricate a thin drug-containing polymer coating on commercially available glaucoma drainage devices such as Ahmed valves. These coatings may be designed to deliver antifibrotic agents (e.g., mitomycin C and/or 5-fluorouracil) into the subconjunctival space and inhibit postoperative fibrosis. In some embodiments, the method involves the creation of films of "breath figure" porous poly (lactic-co-glycolic acid) (PLGA) with incorporated drugs. The breath figure is a method of fabricating a regular arrangement of pores in a polymer film, when the polymer solution is evaporated out under humid conditions. The porous structures can be advantageous in modifying the drug release characteristics and the degradation pattern of the polymer. In some embodiments, to achieve a relatively continuous release of anti-fibrotic activity over a 20-30 day period, a double-layered porous PLGA film is fabricated, in which the more stable 5-FU is dispersed into the bottom layer and the top layer is surface-loaded with MMC. The morphology of embodiments of these films, and their ability to release anti-proliferative drugs and the efficacy of the drugs released from the films using in vitro cytotoxicity assays are discussed herein.

In some embodiments, the disclosure provides a drug delivery device comprising a therapeutic film having one or more layers of polymeric film made by a breath figure technique and a therapeutic agent. In some embodiments, the therapeutic film comprises a single polymeric film layer. In some embodiments, the therapeutic film comprises multiple polymeric film layers. In some embodiments, the therapeutic film comprises a first polymeric film layer associated with a first therapeutic agent. In some embodiments, the therapeutic film further comprises a second polymeric film layer optionally including a second therapeutic agent. In some embodiments the therapeutic film is formed by spin casting an a polymer solution containing the first therapeutic agent (for example spin casting an emulsion containing the first therapeutic agent with a polymer solution) to produce a first polymeric layer, spin casting a second polymeric layer onto the first layer, and thereafter loading a second therapeutic into pores of the second polymeric layer. In some embodiments, the device is configured to provide a glaucoma therapy, for example the device includes a first layer with a first, slower-acting glaucoma agent dispersed therein and a second layer with a second, faster-acting glaucoma agent loaded into pores of the second layer. In some embodiments, the device is configured to provide a treatment for an illness or disease that may benefit from a delivery system that releases drugs on contact with liquid. For example, the the device (which may be simply the single or multi-layer film itself) may include one or more therapeutic agents directed at treating cancer such as a glioblastoma drug including fenofibrate, chemo agents such as temolozomid, vaso inhibitors such as avatsin, imatinib, getifinib, or for example other drugs which may preferentially kill cancer cells as compared to or to the exclusion of normal cells.

In some embodiments, the methods of making a drug delivery device include producing a therapeutic film by using a breath figure technique to produce a first polymeric film layer and associating a therapeutic agent with the first polymeric film layer. In some embodiments, associating comprises spin casting a polymer solution with a therapeutic agent to produce the first polymeric film layer. In some embodiments spin casting a polymer solution with a therapeutic agent involves spin casting a polymer solution together with an emulsion containing the therapeutic agent to produce the first polymeric film layer. In some embodiments, spin casting a polymer solution with a therapeutic agent involves spin casting a polymer solution including the therapeutic agent dissolved or dispersed therein to produce the first polymeric film layer. In some embodiments, associating comprises loading pores of the first polymeric film layer made by a breath figure technique with a therapeutic agent. In some embodiments, methods of making the drug delivery device further comprises spin casting a second polymeric layer on the first polymer layer. In some embodiments, the methods of making a drug delivery device include attaching the therapeutic film to an implantable device such as a glaucoma drainage device, including an Ahmed valve, a Baerveldt tube shut, and including any such device having a plate and a tube.

In some embodiments, the methods involve implanting a drug delivery device as disclosed herein (for example implanting a glaucoma drainage device associated with a therapeutic film according to this disclosure, or for example implanting a therapeutic film) into a patient at a site in need of treatment, wherein a therapeutic agent directed at the desired treatment is released by the drug delivery device in situ. In some embodiments, the drug delivery device is configured for treating glaucoma, for example the drug delivery device includes multi-layered therapeutic, polymeric film having a first polymeric layer associated with a first glaucoma agent and a second polymeric layer associated with a second glaucoma agent attached to a glaucoma drainage device such as an Ahmed valve, and the method involves implanting the device in the subconjunctival space. In some embodiments, the drug delivery device is configured for treating an illness or disease which may benefit from a drug delivery system that releases a drug or drugs on contact with liquid. For example, in some embodiments, the drug delivery device is configured for treating cancer (for example brain cancer, or for example a glioblastoma), such as by associating an anticancer agent (such as fenofibrate, chemo agents such as temolozomid, vaso inhibitors such as avatsin, imatinib, getifinib, and other drugs that can potentially preferentially kill cancer cells as compared to or at the exclusion of normal cells) with the one or more polymeric film layers and the method involves implanting the layered device near the site of the tumor.

In some embodiments, it is an object of this invention to provide a film with a therapeutic agent that may be affixed or implanted into the eye of an animal to treat an eye disease.

In some embodiments, it is another object of this invention to provide an implantable, biodegradable film with a therapeutic agent that can be implanted into an animal to treat a disease. In one embodiment, the devices provide a film that may treat cancer.

In some embodiments, it is another object of the invention to provide a method of creating a therapeutic film comprising spin coating a polymer solution, including at least one therapeutic in a humid environment to produce a breath figure. In another embodiment, a method to create a therapeutic film comprises a dip coating technique that includes aerosolizing a solution to create the film.

Other objects and advantages of some embodiments will become readily apparent from the ensuing description. While the disclosure provides certain specific embodiments, the invention is not limited to those embodiments. A person of ordinary skill will appreciate from the description herein that modifications can be made to the described embodiments and therefore that specification is broader in scope than the described embodiments. All examples are therefore non-limiting. And the various embodiments may include none, some or all of the above-mentioned objects and/or advantages.

BRIEF DESCRIPTION OF THE DRAWINGS

FIG. 24 provides an SEM image showing the porosity of an exemplary film after therapeutic incorporation.

FIG. 25 provides a photograph of a 12-well plate used for exemplary PLGA toxicity test after fixation and toluidine blue staining. The plate shows the control PLGA film toxicity (C, no drug) and the drug loaded PLGA films toxicity against COS-1 cells (0.25, 1 and 5 µg MMC).

FIG. 26 illustrates dose-response of COS-1 cell accumulation in response to PLGA films with different drug loadings. After solubilization of the cell-bound dye (toluidine blue), the color was a measure of the number of viable cells (quantified as absorbance at 650 nm). Tests were used to determine if the samples with MMC were significantly different from the control; *, $p \leq 0.05$, **, $p \leq 1 \times 10^{-8}$.

FIGS. 6A, 6B and 6C shows the cytotoxicity for 0.1, 0.4 and 2 mg 5-FU films in the presence of 1 µg MMC added to the top layer of breath figure film. The figures show the effect of adding MMC to overcome the inconsistency in the toxicity for the initial 5 days.

DETAILED DESCRIPTION

Figure 1:
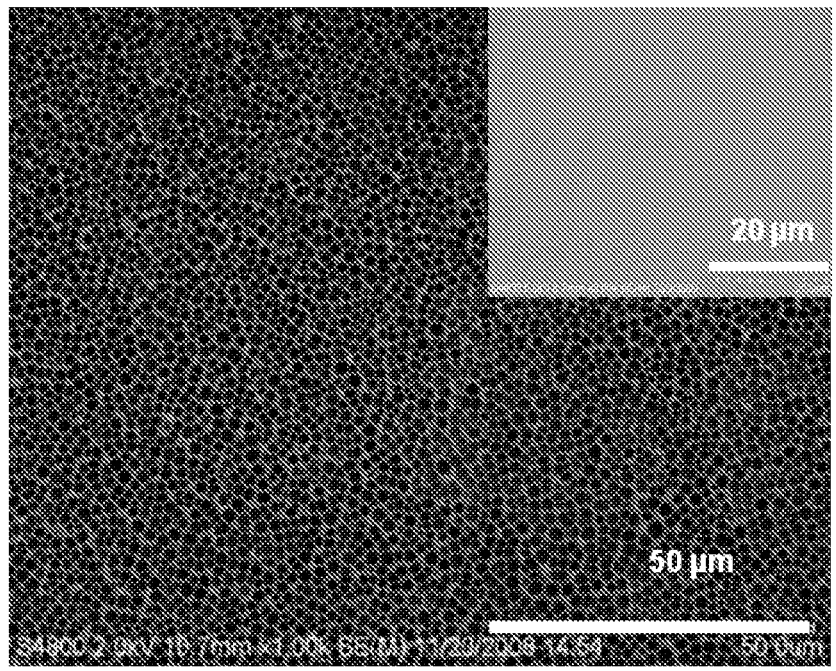
FIG. 1 shows a low magnification scanning electron microscopy (SEM) image of an exemplary breath figure PLGA film's surface topography (Inset: Surface morphology of non-porous PLGA film).

Detailed descriptions of one or more embodiments are provided herein. It is to be understood, however, that the present invention may be embodied in various forms. Therefore, specific details disclosed herein are not to be interpreted as limiting.

Where ever the phrase "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that don't negatively impact the intended purpose. Descriptive terms are understood to be modified by the term "substantially" even if the word "substantially" is not explicitly recited.

The term "about" is meant to account for variations due to experimental error. All measurements or numbers are implicitly understood to be modified by the word about, even if the measurement or number is not explicitly modified by the word "about."

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c.

Where ever the terms "a" or "an" are used, "one or more" is understood, unless such interpretation is nonsensical in context.

The term "animal" should be construed broadly to include human.

The disclosure relates to devices and methods, such as surgical devices and methods, for drug delivery, such as sustained release drug delivery. In some embodiments, the devices are film devices, such as multi-layer film devices. In some embodiments, the devices are multi-layer and/or biodegradable and/or surgical film devices for sustained release drug delivery. In some embodiments, the methods are methods of making the devices, which methods comprise incorporating a therapeutic agent into a film which film is made using a breath figure technique. In some embodiments, the methods of making include incorporating the drug into the film layer during formation of the film, such as during spin coating a polymer solution into a film. In some embodiments, the methods of making include incorporating the drug into the film by loading, for example coating, the drug into the pores of a prepared film. In some embodiments, the methods are methods of using the devices, which methods may comprise implanting the device at a site in a patient in need of treatment and using the device to administer a therapeutic agent in situ. In some embodiments, the methods of using involve implanting a glaucoma drainage device associated with a device in accordance with the disclosure (for example coated with a film device or otherwise attached to a film device in accordance with the disclosure) and using the device to deliver a glaucoma agent in situ. In some embodiments, the methods of using involve implanting the device on, in or nearby tumor of a patient and using the device to deliver a therapeutic cancer drug, for example to shrink or treat the tumor.

In some embodiments, the devices comprise a first polymer layer carrying a therapeutic agent. In some embodiments, the devices comprise a first polymer layer carrying a first therapeutic agent, a second polymer layer optionally carrying a second therapeutic agent, wherein the first polymer layer and the second polymer layer may be the same or different and the first therapeutic agent and the second therapeutic agent may be the same or different. In some embodiments, the devices comprise a first polymer layer carrying a first therapeutic agent, a second polymer layer carrying a second therapeutic agent, wherein the first polymer layer and the second polymer layer may be the same or different and the first therapeutic agent and the second therapeutic agent may be the same or different. In some embodiments the first or second polymer layer, and in some embodiments the first and second polymer layer, are made by a breath figure technique. In some embodiments having a first and second polymer layer including a first and second therapeutic agent, and for example wherein the first and second polymer layer are made using a breath figure technique, one of the layers provides a burst-release of therapeutic agent and the other layer provides a sustained release of therapeutic agent. The multi-layer breath film polymer layer approach to drug delivery (including one or both of a burst release and sustained release drug delivery profile) is suitable for a broad range of target applications (treatments) including without limitation the specific target application examples (glaucoma and brain cancer) discussed herein. For example, the approach may be understood as a delivery system that releases drugs on contact with liquid and thus is suitable for use for other target applications including for treating other cancers and not just brain cancer, for example bladder cancers.

In some embodiments, the polymer layers (e.g. the polymer film layers) comprise a polymer chosen from biodegradable polymers, such as a poly(DL-lactide-co-glycolide) ("PGLA"). In some embodiments, the polymer is PGLA. In some embodiments, the biodegradable polymers substantially or completely degrade away over a period of from about 30 to about 60 days. In some embodiments, the polymer is a biodegradable polymer, for example PGLA, such that the implanted surface seen after completion of wound healing is simply the inert substrate, such as silicone, as the PLGA films completely degrade away over a period of 30-60 days.

In some embodiments, the polymer layers comprise a polymer chosen from biodegradable polymers such as PGLA and a pore-forming agent such as a polyethyleneglycol ("PEG").

In another embodiment, the film is a biodegradable polymer film. In one embodiment, the biodegradable polymer film comprises at least one of the following: gelatin; PLGA porous coating; PLGA/PEG composite porous coating; nonporous PLGA coating; nonporous PLGA/PEG composite coating. In some embodiments, the biodegradable polymer film was created using the breath figure technique.

In some embodiments, the therapeutic agent or drug may be any therapeutic that can be dissolved in the aqueous portion of an oil in water emulsion. In some embodiments, the therapeutic agent or drug may be any therapeutic that can be loaded into pores created in a prepared film. In some embodiments, the devices comprise therapeutic agents that can be dissolved in the aqueous portion of an oil in water emulsion, or therapeutic agents that can be dissolved or dispersed in a polymer solution which may be spun cast using a breath figure technique into a polymeric films for drug delivery according to this disclosure, and therapeutic agents that can be injected into pores created in a prepared film; the therapeutic agents may both be associated with the same layer of a single or multi-layer device or they may be associated with different layers of a multi-layer device.

In some embodiments, the device is a dual layer biodegradable film that provides for a time-release of at least one drug. In further embodiments, the device is a dual layer biodegradable film that provides for a time release of at least one drug and a burst release of at least one drug. In some embodiments, the device is configured to deliver a therapeutic agent, in which the effects of the therapeutic agent may occur over the course of from about twenty to about thirty days. In further embodiments the polymer layers (e.g. the first polymer layer and the second polymer layer) are in the form of a film or coating. In some embodiments, the devices utilize a sandwich design to deliver the drug effectively. For example, in some embodiments, wherein the device comprises a first polymeric layer and a second polymeric layer, the second polymeric layer may be used as a sealant.

In some embodiments, the devices are made from biodegradable polymers which are formed into films using the breath figure technique. For example, the biodegradable polymer is dissolved in a solvent and the polymer solution is spin coated in a humid environment over a substrate such as silicon. In some embodiments, a second polymer is formed into a film by spin-coating a second polymer over a completed film. In some embodiments, the therapeutic agent is associated with the device by dissolving the therapeutic drug in the aqueous part of a water-in-oil emulsion, dissolving a biodegradable polymer in a solvent such as dichloromethane, and spin coating the emulsion and the polymer solution in a humid environment over a substrate such as silicon. In some or further or alternative embodiments, the therapeutic drug is associated with the device by loading (for example coating) the therapeutic into pores of the completed film, such as injected the therapeutic drug in pores over the second completed film (which for example has been spun coated over the first completed film).

In some embodiments, the device is a dual layer device in which the first layer comprises a first drug which is spun coated with the polymer solution to form the first layer, the second layer is spun coated onto the first layer and the second layer comprises a drug which is loaded into the pores of the second layer. In some embodiments, the second layer does not include a therapeutic agent. In some embodiments wherein the first drug is spun coated with the polymer solution, the first drug is dissolved in an oil-in-water emulsion and spun coated with the polymer solution. In other embodiments wherein the first drug is spun coated with the polymer solution and the first drug is water soluble, small particles of the water-soluble drug are suspended in the polymer solution and spun coated.

In some embodiments, the device is configured as a biological surgical film to inhibit the fibrosis that occurs after the implantation of a GDD for treatment of glaucoma. For example, the device is a dual layer device in which the first layer is a PGLA film which is formed by spin-coating 5-flurouracil ("5-FU") dissolved into a polymer (PGLA) solution and the second layer is a PGLA film into which mitomycin C ("MMC") is loaded into the pores of the already-prepared second film layer. In some embodiments the device is prepared by spin coating the first layer onto a glaucoma drainage device such as an Ahmed valve, Baerveldt tube shunt or any GDD including a plate and a tube. In some embodiments, the prepared device (the prepared multi-layer film) is attached to a glaucoma drainage device to help treat glaucoma. For example, in one embodiment the film (e.g. the multi-layer film) is attached to the glaucoma drainage device using a string made of biodegradable polymer. In another embodiment, the film is attached to the glaucoma drainage device using a biocompatible glue.

In embodiments wherein the device is configured as a biological surgical film for the treatment of glaucoma, methods of use include placing the Ahmed valve or other glaucoma drainage device that are associated with the device (for example placing the PGLA-coated Ahmed valve) in the subconjunctival space. In some embodiments, the slow drug release (for example of the 5-FU spun coated with the first layer) surrounding the end plate may prevent occurrence of an inflammatory reaction after surgery. The release of drug from the coating may be triggered by the aqueous humor drained out of the anterior eye by the valve. Thus, in some glaucoma drainage devices ("GDD"), the device uses two therapeutics (e.g. MMC and 5-FU), with a small dose of MMC to provide the initial burst release to prevent fibroblast growth in the critical period immediately after surgery. The slow release of the less potent 5-FU over longer time periods may allow the wound healing to progress without scarring and blockage of the drainage conduit from the Ahmed valve.

Examples provided herein demonstrate that GDD embodiments of the disclosure may enable the use of two therapeutics, such as MMC and 5-FU, to provide an initial burst to prevent fibroblast growth in the critical period immediately after surgery and then a slow release over longer time intervals while wound healing progresses, thus eliminating or alleviating scarring and blockage of the drainage conduit from the Ahmed valve and the thickening of the wall of the subconjunctival tissue through which the fluid drains. Examples herein provide results which indicate that the two therapeutics (MMC and 5-FU) work in tandem to inhibit fibroblast growth for a period of about 3-4 weeks during which wound healing occurs. Without wishing to be bound by theory it is believed that the use of breath figure morphologies facilitates release, and the design of layered structures with PGLA films is eminently feasible allowing multiple combinations of fast and slow release with multiple drug species and the use of drug-free layers as sealants to control initial bursts.

In another embodiment, the prepared film is attached near the tumor of a patient in order to shrink the tumor or treat cancer. For example a device comprising a PGLA film loaded with an anticancer therapeutic agent such as fenofibrate may be surgically inserted at a site in need of treatment. For example, fenofibrate may be incorporated into a wafer of PGLA, which wafer may be placed directly in the cavity after the brain tumor resection. Examples herein demonstrate embodiments of fenofibrate/polymer film anticancer approaches according to this disclosure. Other examples may include other cancers where fluid is present at or near the tumor site (e.g., bladder cancer) and other therapeutics for treating the exemplified or other cancers.

EXAMPLES

Materials and Methods

Poly (D,L-lactide-co-glycolide) (PLGA 50:50) polymers, Resomer RG 504 ($M_w$=56,000; Inherent viscosity=0.56 dl/g) and Resomer RG 506 (Mw=96,000; Inherent viscosity=0.80 dl/g) were purchased from Boehringer Ingelheim Chemicals Inc., (Petersburg, Va.). Methylene chloride (ACS grade) was obtained from Fisher Scientific, USA. Ahmed glaucoma valves (Model FP7) and the medical grade silicone sheets from which these valves were manufactured were generous gifts from New World Medical Inc. (Rancho Cucamonga, Calif.). Mitomycin C (MMC) (derived from *Streptomyces caespitosus*), 5-fluorouracil (5-FU), neutral buffered formalin and toluidine blue were from Sigma Aldrich Chemicals (St Louis, Mo.). Transwells® with 12 mm 0.4 μm pore polyester membrane inserts and 12-well Costar tissue culture plates were purchased from Corning (Wilkes Barre, Pa.). COS-1 cells were obtained from the American Type Culture Collection (Manassas, Va.) and maintained in a humidified atmosphere of 5% $CO_2$/95% air in glutamine-free DMEM (4500 g/L glucose and 1.5 g/L sodium bicarbonate) supplemented with 10% fetal bovine serum, 4 mM glutamine, 1 mM sodium pyruvate, 100 IU/mL penicillin, 100 μg/mL streptomycin and 0.25 μg/mL amphotericin B. Fetal bovine serum was purchased from Atlanta Biologicals (Lawrenceville, Ga.). Dulbecco's Modified Eagle's Medium (DMEM), L-glutamine, antibiotic-antimycotic solution, and sodium pyruvate were from Life Technologies (Grand Island, N.Y.). All chemicals were used as received, without further purification.

Example 1: Synthesis of "Breath Figure" PLGA Polymer Films

Example 1A: Synthesis of 'Breath Figure' PGLA Polymer Films with a Teflon Substrate In one embodiment, a spin coater (model WS-400-6NPP-LITE, Laurell Technologies Corporation, North Wales, Pa.) was used to prepare the film. A 1.5 cm square piece of teflon, used as the substrate was rinsed with 95% ethanol to remove any surface contaminants. The substrate was then placed on the spin table which is connected to a vacuum to hold the substrate while spinning. The coating chamber is connected to a flow of humid air created by bubbling the air through the distilled water. Although the humidity can be modified by mixing the air with dry nitrogen, in our experiments, we maintained the relative humidity at about 70% as measured by a hygrometer (Fisher Scientific).

Figure 18:
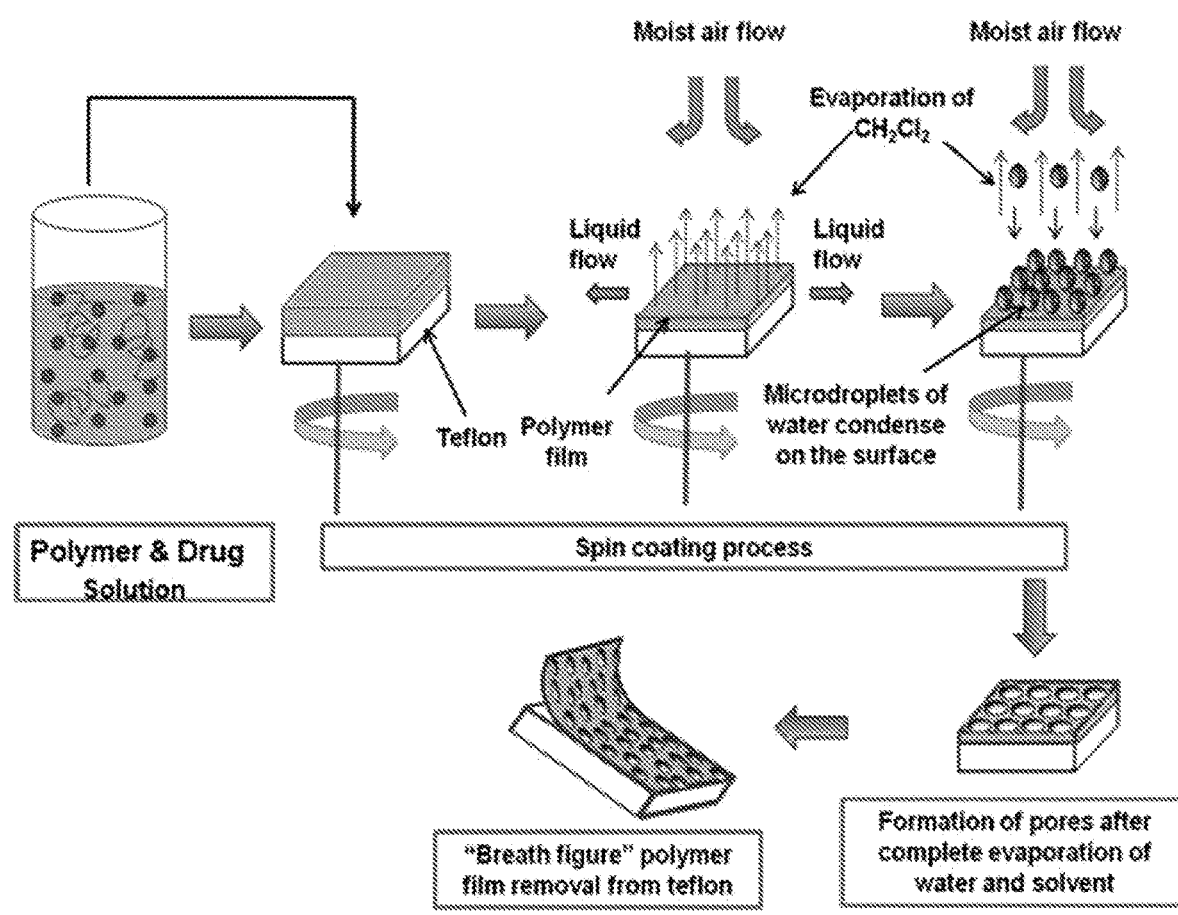
FIG. 18 illustrates an exemplary mechanism of incorporating a drug into a thin PLGA film by 'breath figure' and spin coating technique.

FIG. 18 illustrates the entire process of breath figure thin film fabrication. To prepare the coating solution, 1% (w/v) of a drug (e.g., Ibuprofen, Salicylic acid) was first dissolved in methylene chloride followed by dissolving 15% (w/v) of the PLGA polymer. The solution was vortex mixed to ensure homogeneity. The appropriate volume (0.4 mL) of the solution containing PLGA and the drug (67 μg drug/mg polymer) was dropped onto the substrate and the spinning process was immediately accelerated to 2500 rpm for 30 sec. During the spin coating process, the solvent evaporates to form an opaque film. The coated films were dried for at least a day at room temperature. In experiments with PEG, the ratio of PEG to PLGA was 1:9. Similar procedures were followed to prepare control breath figure films without the drug component. To prepare non porous films, the gas supply was switched from humid air to dry nitrogen. All films were easily peeled off from the teflon substrate. To clearly obtain release and morphological characteristics from breath figure coated systems, the films were reattached to teflon squares using double-sided tape (3M). This ensures that both release and degradation will occur primarily from the porous surface of the film.

Example 1B: Synthesis of "Breath Figure" PLGA Polymer Film with a Silicone Substrate In another embodiment, a spin coater (model WS-400-6NPP-LITE, Laurell Technologies, North Wales, Pa.) was used to prepare thin PLGA films with a microporous structure. Using a trephine, discs were cut from medical grade silicone sheets identical to those used in the manufacture of the Ahmed valves. The discs were rinsed with distilled water and 95% ethanol to remove any surface contaminants. The discs were then placed on the spin turntable, which was subsequently connected to a vacuum line to hold the substrate in place while spinning. In order to maintain high relative humidity, the spin coating chamber was connected to a flow of humid air created by bubbling the air through distilled water. A relative humidity of at least 70% (measured using a hygrometer) was maintained in the chamber during all spin coatings. The films were dried at room temperature.

In this embodiment, the PLGA polymer was dissolved in methylene chloride at a concentration 15% (w/v). A specific volume of 75 μL of the polymer solution was dropped onto the silicone substrate and spun at 2500 rpm for 30 sec. During the spin-coating process, the rapid evaporation of the solvent causes a cooling effect on the polymer solution surface. The cooling induces the condensation of water droplets (from humid air) onto the solution surface. Micron-sized water droplets nucleate on the surface and subsequently grow to form the arrays of 'islands' that eventually produces the breath figure pattern. These arrays do not coalesce, but penetrate into the polymer solution, which acts as a substrate for subsequent condensation and nucleation of water droplets. The polymer film forms around water droplet/solution interface and encapsulates the water droplets preventing coalescence. Locally acting lateral capillary forces and convective motion resulting from temperature gradients on the solution surface stabilize the water droplets arranging in an ordered manner. Once the film is dried at room temperature, the evaporation of residual solvent and water leads to the formation of a surface patterned with a microporous structure. The breath figure process is simple, economically viable and easily reproducible leading to the formation of an ordered pore structure on the film surface with a dense under layer.

Example 2: Morphological Characterization of Breath Figure Polymer Film

Example 2a: Morphological Characterization of Breath Figure Polymer with a Teflon Substrate Morphological characterizations of all films were done using a field emission scanning electron microscopy (FE-SEM; Hitachi S-4800) at an accelerating voltage of 3 kV. The films were mounted on the SEM sample holder and gold coated using a sputter coater (Polaron SEM coating system) set at 20 mA for duration of 75 sec. All films were imaged in the dry state which is appropriate for PLGA films which in contrast to hydrogels, do not absorb water significantly and therefore do not change morphology.

Example 2B: Morphological Characterization of Breath Figure Polymer with a Silicon Substrate The morphology of uncoated silicone and breath figure PLGA-coated samples was characterized using field emission scanning electron microscopy (Hitachi S-4800) as previously described (Ponnusamy T, Lawson L B, Freytag, L C et al. In vitro degradation and release characteristics of spin coated thin films of PLGA with a "breath figure" morphology. *Biomatter.* 2012; 2:77-86). All samples were coated with a thin layer of gold using a sputter coater (Polaron SEM coating system) prior to imaging. Both the pore dimensions and the thickness of coatings were examined.

Example 2C: Surface Contact Angle

The wettability of breath figure films was measured using the sessile drop method with a standard goniometer (Rame-Hart model 250) and analyzed using the DROPimage Advanced software for contact angle determination. A 3 μL distilled water droplet was placed on the polymer film surface and the contact angle 'θ' measured. The measurement was done for a minimum of 5 samples of a specific polymer film, and the average value reported. Typical standard deviations are of the order of 0.3.

Example 2D: Discussion

Figure 21:
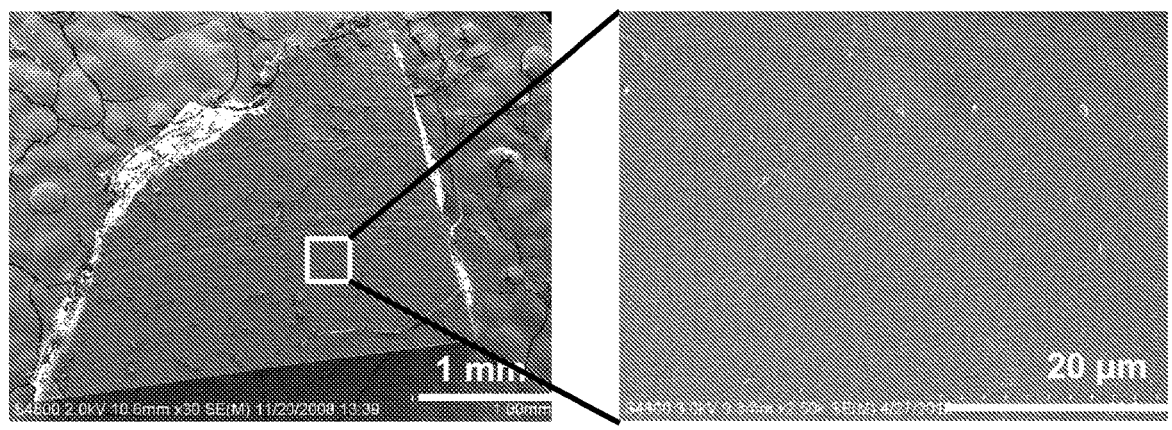
FIG. 21 shows scanning electron microscopy images, at low and high magnification, of an uncoated medical grade silicone surface.
Figure 22:
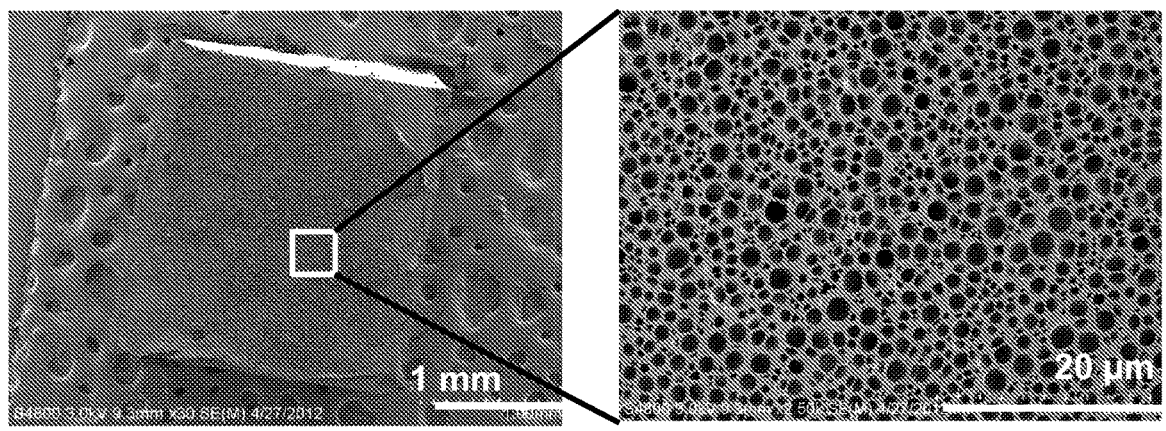
FIG. 22 shows scanning electron microscopy images, at low and high magnification, of silicone coated with porous PLGA film on the surface.

When PLGA is spin coated onto a solid substrate, the rapid evaporation of the carrier solvent causes a cooling effect on the polymer solution surface and this cooling induces the condensation of water droplets (from humid air) onto the solution surface. Micron-sized water droplets nucleate on the surface and subsequently grow to form arrays of 'islands' that eventually produce the breath figure pattern. Locally acting lateral capillary forces and convective motion resulting from temperature gradients on the solution surface stabilize the water droplets, allowing them to arrange in an ordered manner. When the film is dried at room temperature, the evaporation of residual solvent and water leads to the formation of a surface patterned with a microporous structure atop a dense underlayer, as shown in FIGS. 21 and 22. FIG. 21 illustrates the smooth surface of the silicone substrate over which the porous PLGA breath figure is spin coated. The PLGA film coating shown in FIG. 22 illustrates the highly porous honeycomb structure of the breath figure.

Figure 2:
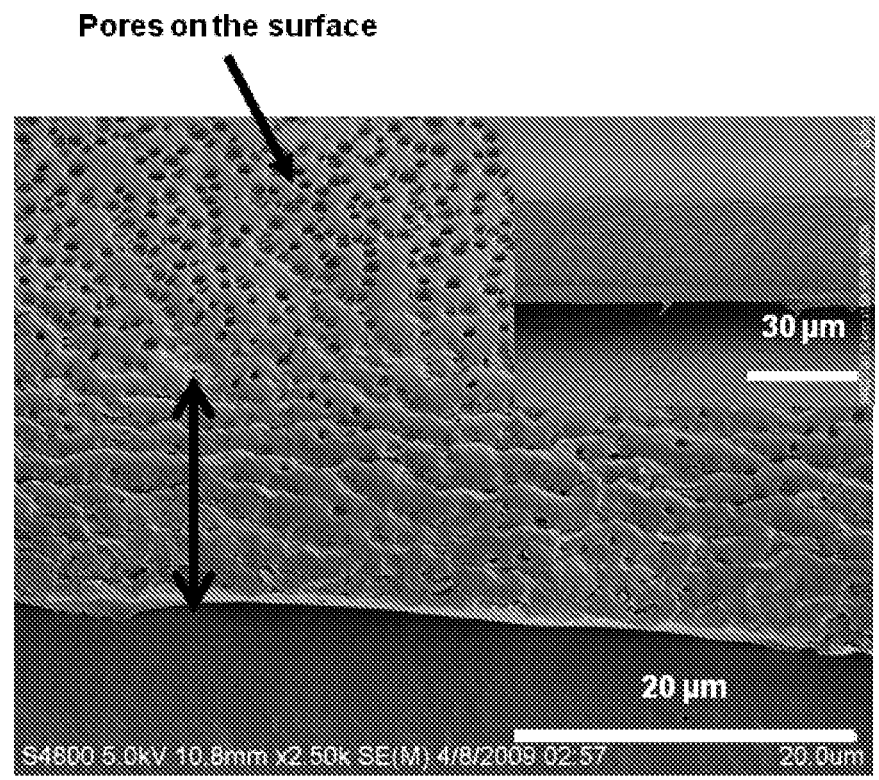
FIG. 2 shows a low magnification SEM image of an exemplary breath figure PLGA film's cross-sectional view (Inset: Cross-sectional morphology of non-porous PLGA film).

FIGS. 1 and 2 show morphological details of breath figure PLGA films in comparison to the nonporous films obtained by spin coating in a dry atmosphere (shown as corresponding insets to the figures). The Scanning Electron Microscope (SEM) image in FIG. 1 reveals an ordered array of approximately 2 μm sized pores on the surface, observed over a large surface area with no defects in the pattern. The pores created from PLGA are highly reproducible and simple to create. FIG. 2 is an oblique view of the cross section and the surface and reveals both surface features and aspects of bulk porosity. Clearly, the pore structure is prevalent almost throughout the film but ends in a dense bottom layer of around 2 μm thickness. The average thickness of the film measured by micrometer is 20 μm.

Figure 3:
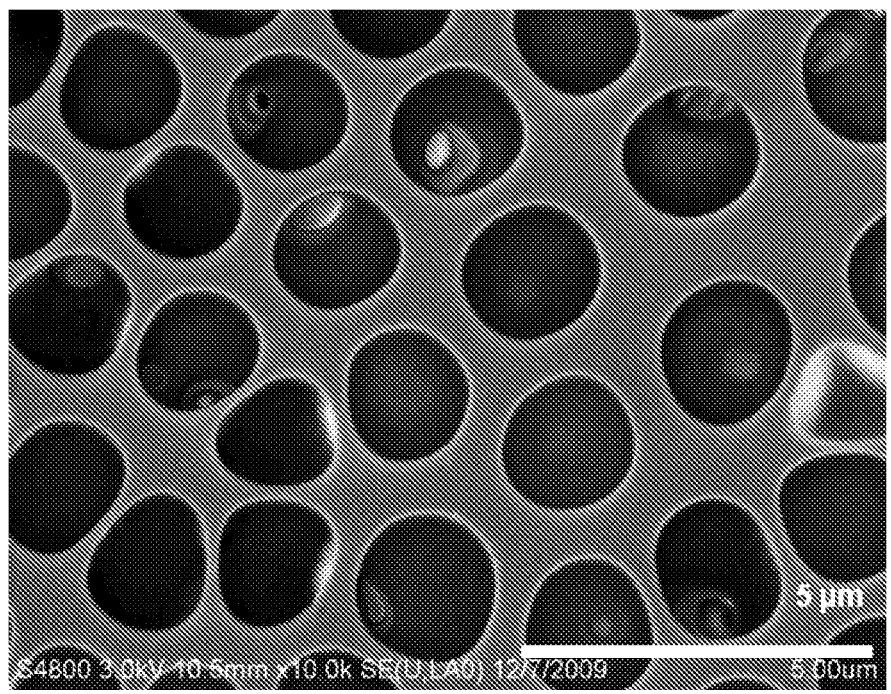
FIG. 3 shows a high magnification SEM image of an exemplary breath figure PLGA film's surface morphology.
Figure 4:
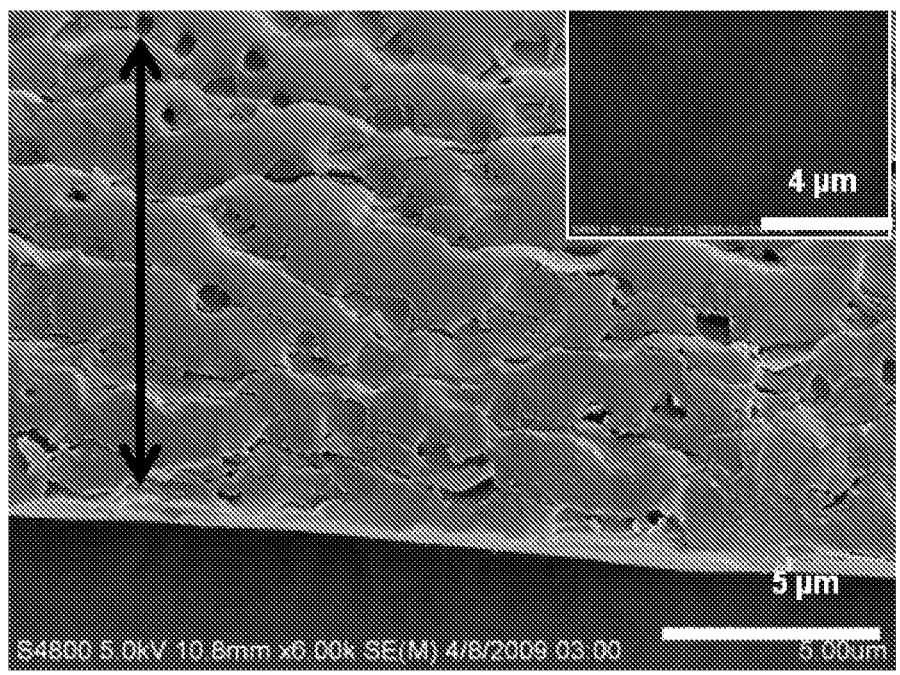
FIG. 4 shows a high magnification SEM image of an exemplary breath figure PLGA film's cross-sectional morphology (Inset: surface morphology of dense bottom layer).

FIGS. 3 and 4 reveal higher magnification of the top and oblique views of the PLGA breath figure. After peeling off the film from the teflon substrate, the dense bottom layer was imaged showing the lack of any discernible pores (inset to FIG. 4).

Figure 5:
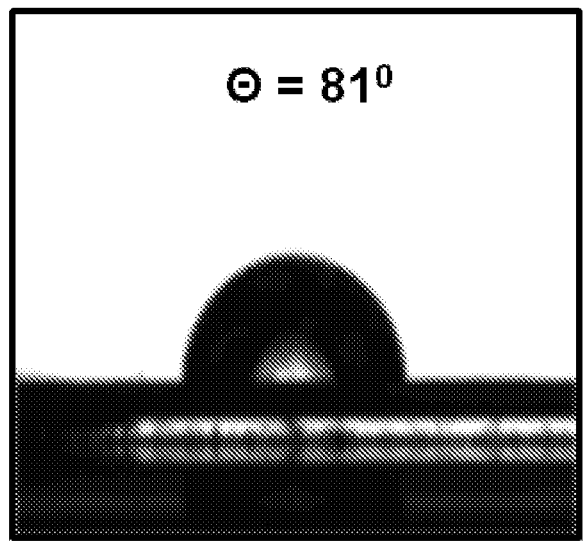
FIG. 5 shows a high magnification SEM image of an exemplary breath figure PLGA film's contact angle of breath figure PLGA film.
Figure 6:
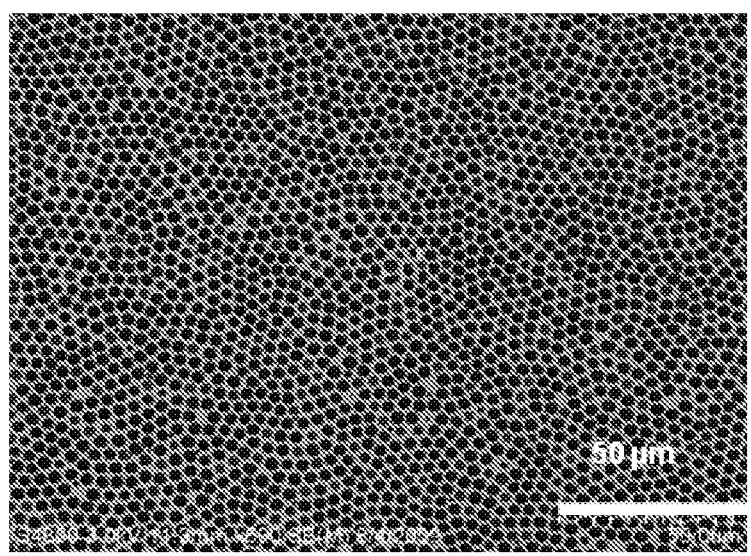
FIG. 6 shows a low magnification SEM image of an exemplary breath figure PEG/PLGA film's surface morphology.

We used the analysis described by Bolognesi (Bolognesi A, Mercogliano C, Yunus S, Civardi M, Comoretto D, Turturro A. Self-organization of polystyrenes into ordered microstructured films and their replication by soft lithography. Langmuir. 2005; 21:3480-5.), to understand pore penetration in the bulk polymer film. Pore formation can be described through the minimization of the free energy at the 3 phase (water droplet, air, polymer solution) interface, with a dimensionless pore penetration $Z_0=Z/R$ where Z is the distance of the droplet center from the air-solvent interface and R is the droplet radius. $Z_0$, the value of Z at which the free energy is minimized is expressed as, $$Z_0 = \frac{\gamma_w - \gamma_{w/s}}{\gamma_s} \quad (1)$$

where $\gamma_w$ and $\gamma_s$ are the surface tensions of the air-water interface and the air-solvent interface, respectively, and $\gamma_{w/s}$ is the interfacial tension between water and the solvent. For values $-1<Z_0<1$, the water droplets will locate at the interface between air and solution with partial exposure to both fluids. Upon formation of the final breath figure morphology, such systems will only consist of a single layer of pores below which is a dense nonporous layer. For $Z_0$ values greater than unity, the droplets will penetrate below the surface, the consequence of which is a multi-layered porous polymer structure. For the PLGA-methylene chloride system, $Z_0$ is 1.62, based on the interfacial parameters the water ($\gamma_w$=72.8 dynes/cm), methylene chloride ($\gamma_s$=28.12 dynes/cm) and water-methylene chloride ($\gamma_{w/s}$=27.2 dynes/cm) system. The deep penetration of pores in the PLGA system is due to the penetration of water droplets below the solvent-air interface. FIG. 5 shows the droplet shape for contact angle determination of breath figure PLGA, from which a value of 81° was obtained, indicating relative hydrophobicity of the material.

Figure 7:
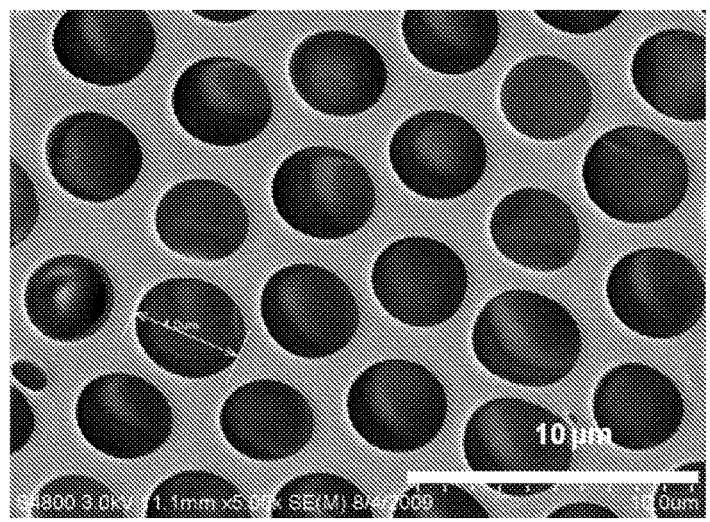
FIG. 7 shows a high magnification SEM image of an exemplary breath figure PEG/PLGA film's surface morphology.
Figure 8:
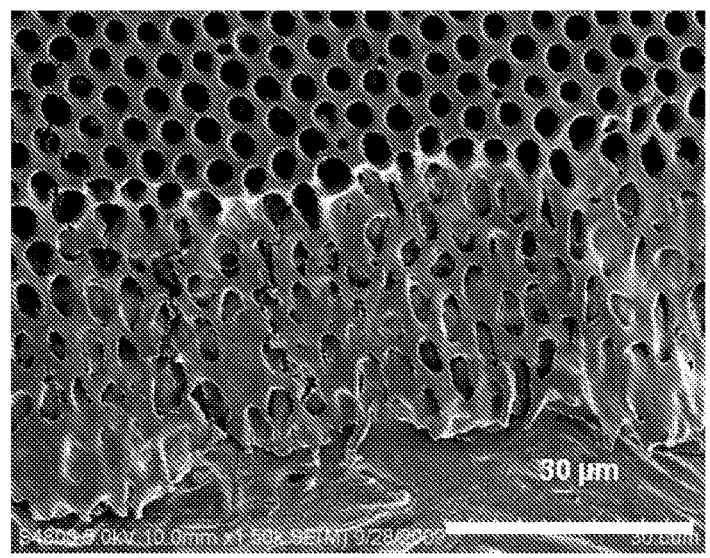
FIG. 8 shows an SEM image of an exemplary breath figure PEG/PLGA film's cross-sectional morphology.
Figure 9:
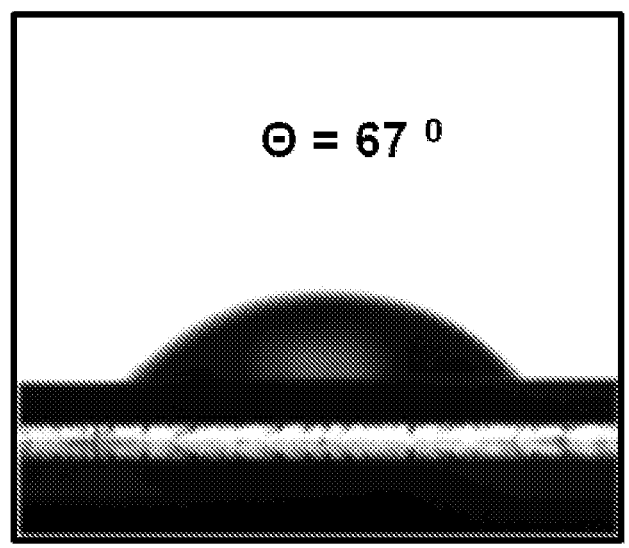
FIG. 9 shows an SEM image of an exemplary breath figure PEG/PLGA film's contact angle of breath figure PEG/P LGA film.

We have found that PEG incorporation leads to a much better definition of pore structure, as shown in FIGS. 3 and 7, and an enhanced hydrophilicity. FIGS. 6-9 illustrate the influence of PEG addition at a 1:9 ratio of PEG to PLGA. The pore structure is highly monodisperse with the pores arranged in ordered hexagonal arrays. The addition of small quantity of PEG molecule has greatly improved the degree of ordering and orientation of pores. Again, we see deep penetration of pores into the polymer film (FIG. 8) with an almost row-by-row arrangement. Our experiments indicate that the optimal PEG incorporation level is approximately 10 wt % and when PEG is added to values greater than 15 wt %, the film tends to become patchy (data not shown for brevity). FIG. 9 indicates that the PEG incorporated breath figure has enhanced hydrophilicity as shown by a contact angle of 67°.

Example 3: In Vitro Degradation of Breath Figure Polymer Film

Experiments to understand the in vitro degradation of breath figure PLGA and PEG/PLGA films were done at 37° C. in phosphate buffered saline solution (PBS) (137 mM NaCl, 2.7 mM KCl, 10 mM Sodium Phosphate dibasic and 2 mM Potassium Phosphate monobasic). The pH was then adjusted to 7.4 using 0.1M HCl. The films coated on teflon were suspended and incubated in the buffer solution for 35 days, and subjected to slow stirring using a magnetic stir bar. The PBS medium was changed every week to maintain constant pH. Each week, a small piece of polymer film was cut from the original film, rinsed carefully with distilled water and dried at room temperature for at least a day prior to imaging.

Example 3A: PGLA Films

Figure 10:
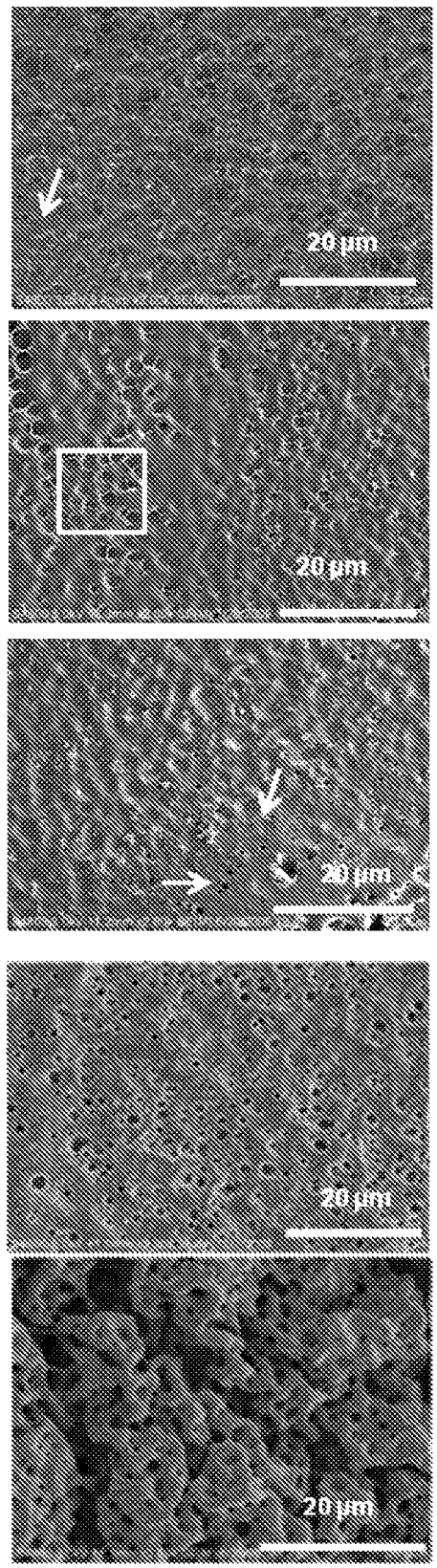
FIG. 10 shows the surface morphology of an in vitro degradation pattern of an exemplary breath figure PLGA film.
Figure 11:
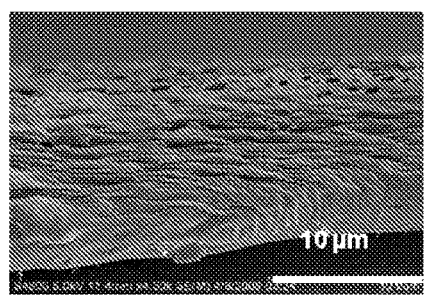
FIG. 11 shows the cross-sectional morphology of an in vitro degradation pattern of an exemplary breath figure PLGA film.
Figure 11:
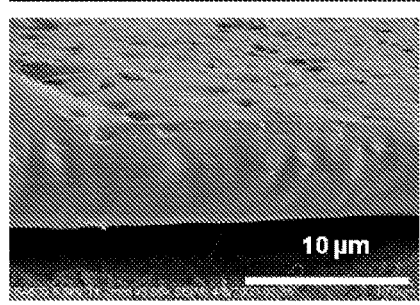
Figure 11:
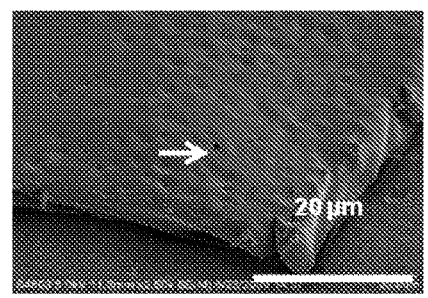
Figure 11:
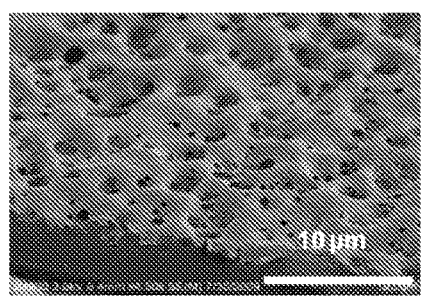
Figure 11:
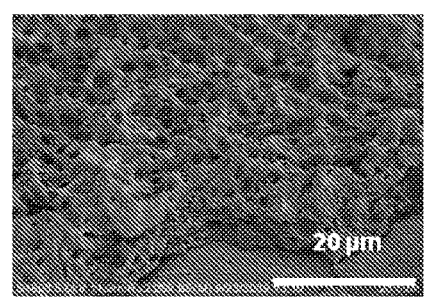

FIGS. 10-11 illustrate the morphological characteristics of the degradation of a breath figure film over a period of 35 days. To simulate an environment where the film is used as a coating, we examined teflon coated films so the degradation is primarily through the porous breath figure surface. Within 7 days, clear morphological changes were observed with the deterioration of the top layer of pore walls leading to a flatter topology as shown by the arrow in FIG. 10 (day 7). The side view (FIG. 11, day 7) also illustrates that the film has significantly decreased in thickness to 5-10 μm. With time, the pores in the lower layers of the original film become revealed as the polymer surface continues to degrade (box in FIG. 10, day 14). We note however that as degradation proceeds to the vicinity of the originally dense non porous bottom layer, small submicron pinprick pores are generated that are not part of the original breath figure structure. The number density of these pinprick pores increase (after 28 days) and the film begins to break up. In 35 days, cracks and islands of macroporous film remnants are observed. The surface of the film also becomes wrinkled. We find that throughout the degradation process, the film continues to adhere to the teflon substrate.

Example 3B: PEG/PGLA Films

Figure 12:
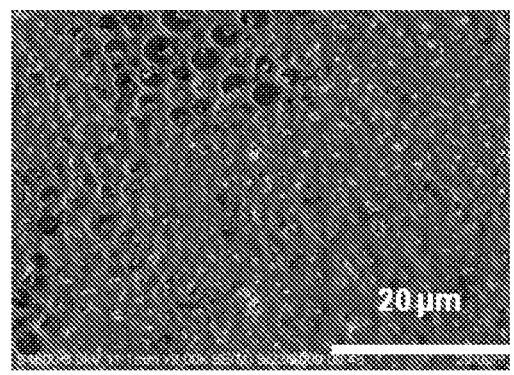
FIG. 12 shows the surface morphology of an in vitro degradation pattern of an exemplary breath figure PEG/PLGA film.
Figure 12:
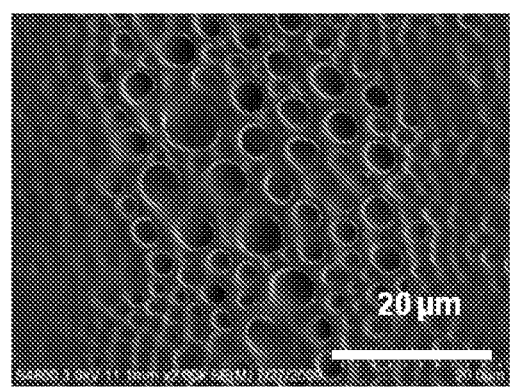
Figure 12:
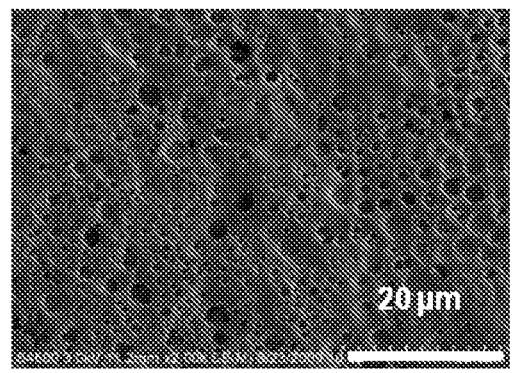
Figure 12:
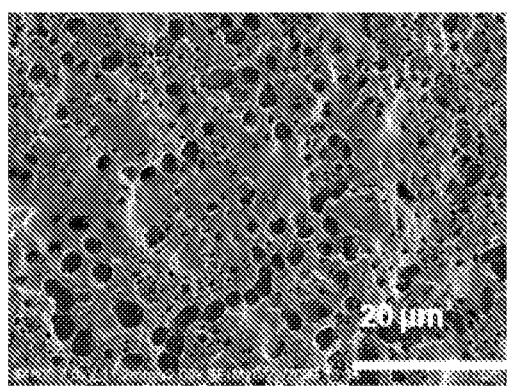
Figure 13:
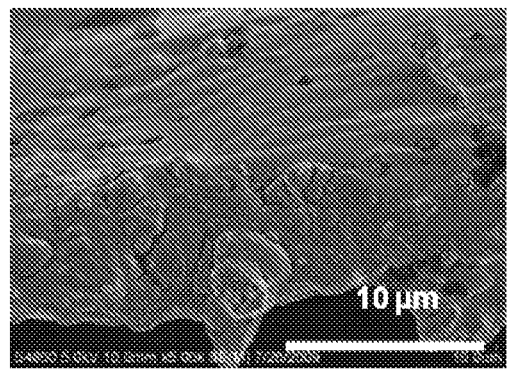
FIG. 13 the cross-sectional morphology of an in vitro degradation pattern of an exemplary breath figure PEG/PLGA film.
Figure 13:
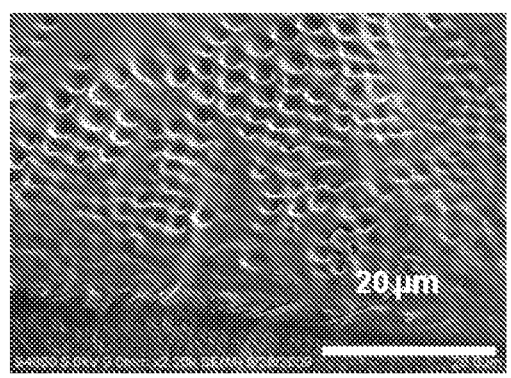
Figure 13:
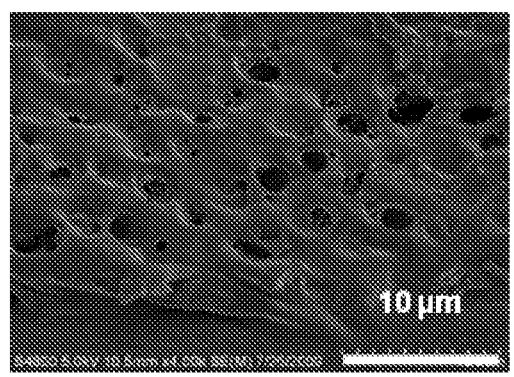
Figure 13:
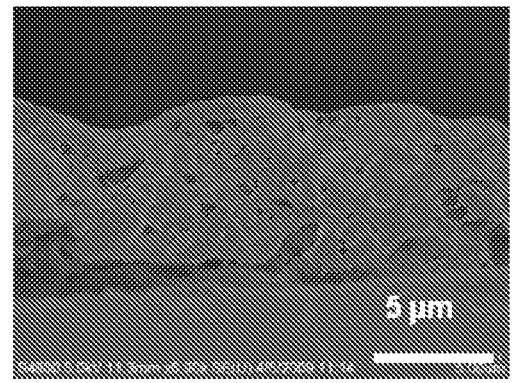

FIGS. 12 and 13 show the effect of PEG in the degradation of PLGA film. Essentially the same progression of deterioration is observed with an initial surface flattening, the revealing of underlying pores, and the eventual formation of new pinprick pores that grow and eventually rupture the film. The addition of PEG may increase the degradation rate as we observe the initial morphological change of underlying pores coming into view is apparent within 7 days of degradation.

Example 4: In Vitro Release Characteristics

Figure 19:
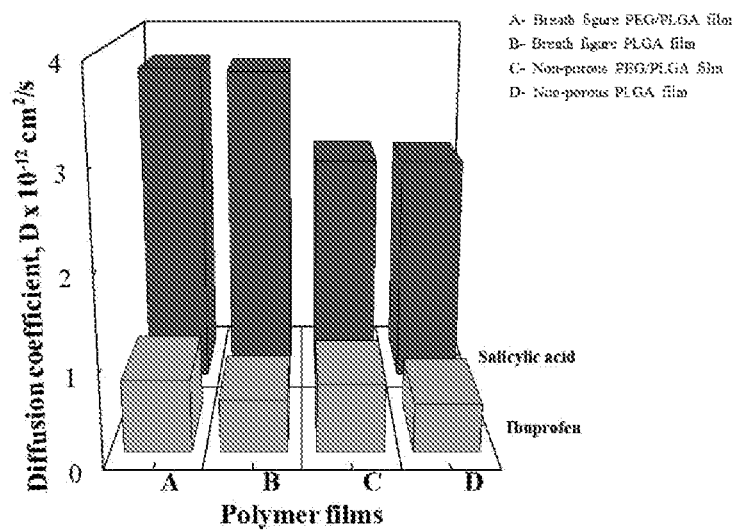
FIG. 19 shows the diffusion coefficients of salicylic acid and ibuprofen for breath figure and non-porous films.

The release of the two model drugs was compared in the porous and non-porous films. The release of the drugs was higher in porous films than the non-porous films; this was attributed to the higher diffusion of drug through water-filled pore cavities. Drug release was also compared in porous film prepared in the presence and absence of PEG, and we found that the release was accelerated by the addition of hydrophilic PEG. By plotting the fractional drug released with respect to square root of time, the kinetic constant obtained for the breath figure PEG/PLGA and PLGA was determined to be 0.1291 h$^{-1}$ ($R^2$=0.9236) and 0.1284 h$^{-1}$ ($R^2$=0.9368), respectively. For the non-porous films, the release constant was 0.1088 h$^{-1}$ ($R^2$=0.9417) and 0.1086 h$^{-1}$ ($R^2$=0.9831) for PEG/PLGA and PLGA, respectively. The drug release data for salicylic acid, a hydrophilic low molecular weight pharmaceutical, and ibuprofen, a hydrophobic low molecular weight pharmaceutical, are summarized in FIGS. 15 and 19. From the diffusion coefficients calculated for both breath figure and non-porous films (shown in FIG. 24), it is apparent that the breath figure films enhance the rate of drug release, as compared to spin-cast, solid PLGA films.

Ibuprofen and Salicylic acid were used as model drugs to characterize the release profiles of breath figure polymer films. The equivalent non-porous smooth films were used as controls. In vitro release studies were carried out by incubating 1.5 cm side square drug incorporated films in 15 ml of PBS medium at 37° C. and stirred gently using a magnetic stirrer. At specific time intervals, 0.650 ml aliquots of the solution was withdrawn and centrifuged to remove any possible debris from the degrading polymer. Then, the aliquot was returned to the vial after measuring the absorbance to quantify drug release. The pH of the medium was monitored during the course of the experiment to verify that the solution is buffered adequately during polymer degradation. Ibuprofen and salicylic acid release were quantified through the absorbance at 221 and 296 nm, respectively. Standard calibration plots of ibuprofen and salicylic acid absorbance were constructed to correlate absorbance with drug release levels. All experiments were conducted in triplicate.

Figure 14:
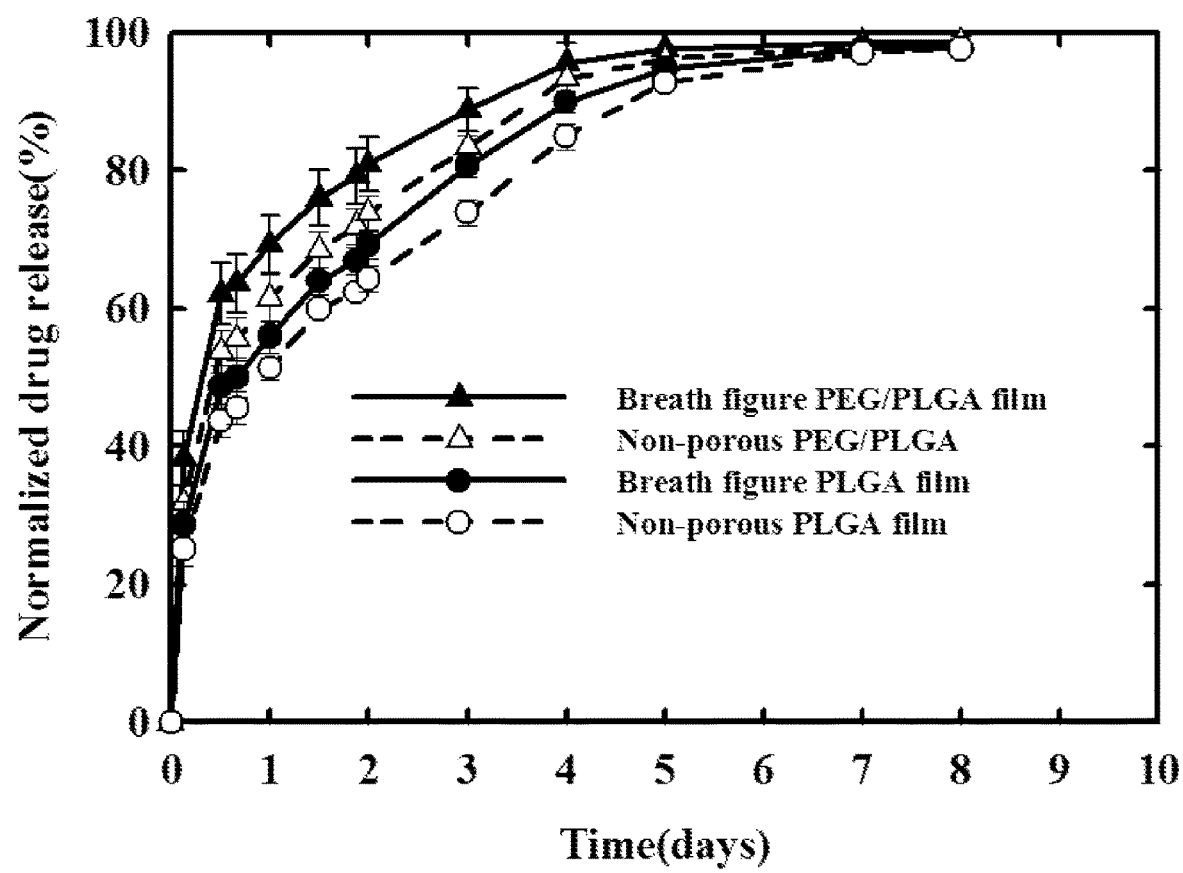
FIG. 14 illustrates in vitro release kinetics of salicylic acid from exemplary breath figure PLGA and PEG/PLGA films.
Figure 16:
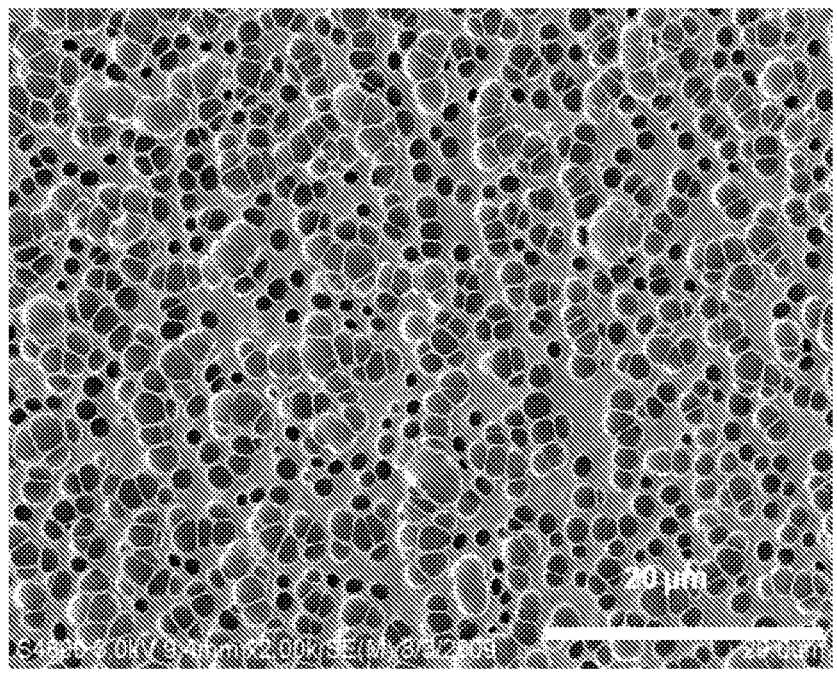
FIG. 16 shows an SEM image of an exemplary breath figure PLGA film after 2 days of incubation.
Figure 17:
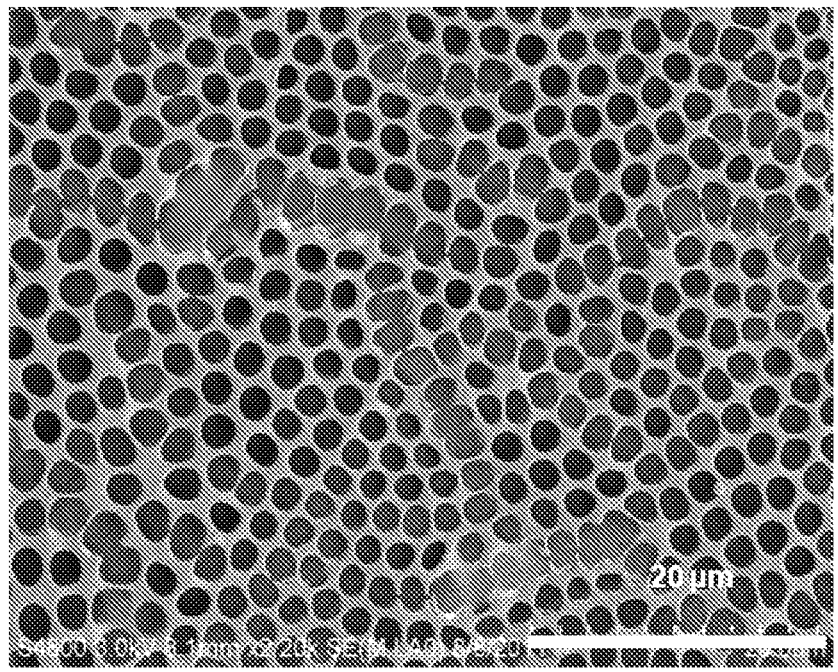
FIG. 17 shows an SEM image of an exemplary breath figure PEG/PLGA film after 2 days of incubation.

The release profile of breath figure PLGA and PEG/PLGA films was carried out in PBS medium (pH 7.4, 0.1M), incubated at 37° C. A non-porous film with the equivalent amount of drug dispersed was used as control. The choice of salicylic acid as a model drug component is due to its high water solubility (>2 mg/mL) and clearly measurable UV absorbance at 296 nm. FIG. 14 illustrates the cumulative release of salicylic acid from the PLGA film and PEG/PLGA film, respectively, for a period of 2 days. The release illustrates the effects of breath figure morphology and the role of incorporating PEG into the film. We note that within 3 hours, differences between the breath figures and the non porous films and between PLGA and PEG/PLGA films are observed and these differences become more pronounced at later times. After 3 hours, all films with the breath figure morphology show a higher release rate than the corresponding non breath figure. The breath figure film reveals the surface pores are not undergone extensive pore deterioration in 2 days of incubation (shown in FIG. 16 and FIG. 17). Upon contact with the aqueous medium, the hydrophilic salicylic acid (Mol. Wt=138.12 g/mol) diffuses out through water filled pores that has higher surface area on the surface. C. S. Proikakis and coworkers (Proikakis C., Tarantili P., Andreopoulos A., The Role of Polymer/Drug Interactinos on the Sustained Release from poly(dl-lactic acid) tablets, European Polymer Journal, 2006; 42: 3269-76), have stated that the repulsive anionic interaction between salicylic acid and carboxylic acid group of poly(lactic acid) enhances release rate at higher pH i.e., 7.4. Additionally, the incorporation of PEG into the films shows an increase in release rate compared to the films with no PEG.

Figure 15:
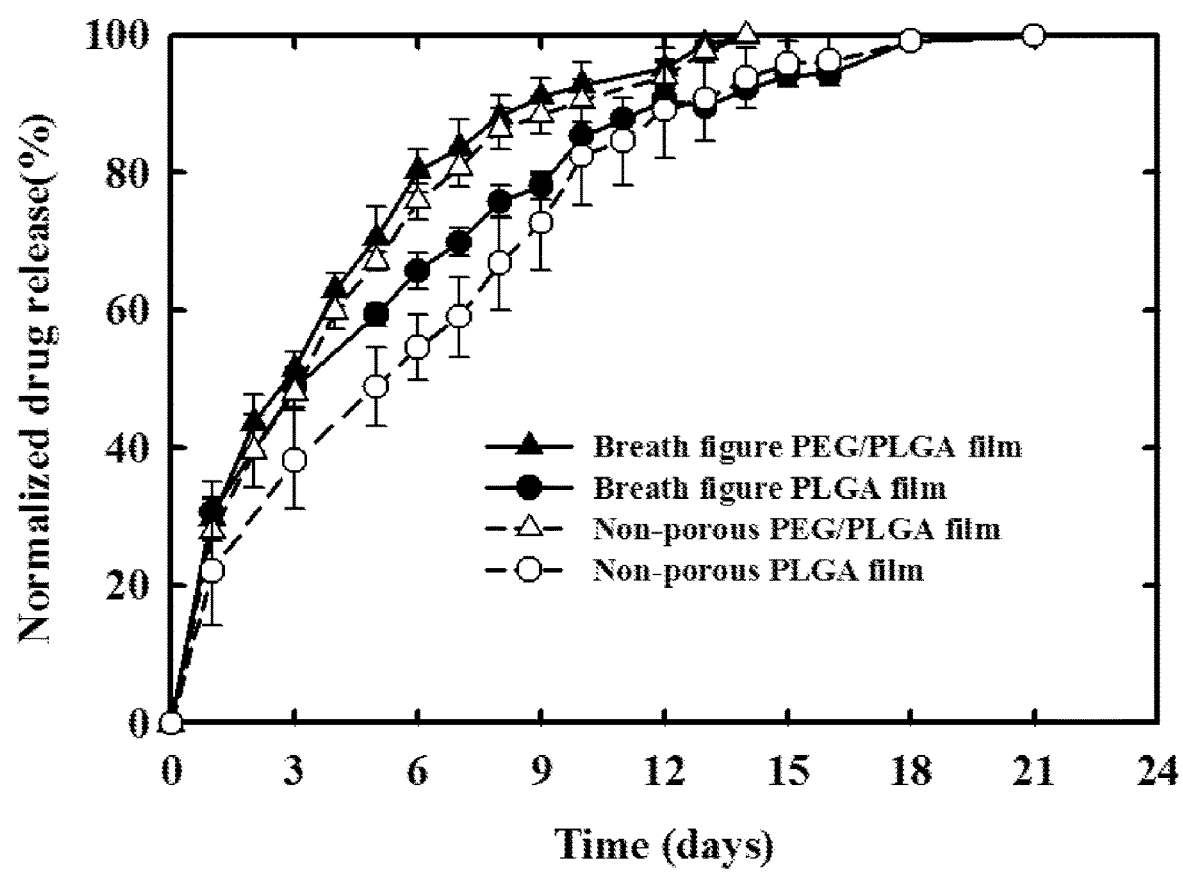
FIG. 15 illustrates in vitro release kinetics of Ibuprofen from exemplary breath figure PLGA and PEG/PLGA films.

The other model drug component, ibuprofen is chosen due to its low water solubility (<0.5 mg/ml). The release kinetics is shown in FIG. 15 for the breath figure films, with non-porous films as control. The release behavior is slower than salicylic acid, which lasts for at least 14 days. As expected, the breath figure films showed an increased rate comparatively with their corresponding non-porous films. However, the non-porous PEG/PLGA film releases the drug higher than the breath figure PLGA film. Upon 7 days of release, the percentile release of non-porous PEG/PLGA film is 81% as compared to 70% rate for the breath figure PLGA film. From the degradation pattern, the morphological change for the breath figure PEG/PLGA film is apparent in 7 days (FIGS. 12 and 15_day 7) as compared to the PLGA film, which still contains porosity for the same corresponding 7 days (FIGS. 10 and 11_day 7). This indicates the slow degradation of PLGA limits the release rate as compared to the film incorporated with PEG. Moreover, the PEG incorporated films reached the equilibrium in less than 14 days.

Example 5: Model Stidy—Breath Figure PLGA Films for Glaucoma Drainage Devices

A variety of formats, including one or more of anti-fibrotic agents, Mitomycin C(MMC) and 5-Fluorouracil (5-FU), were tested in the adaptation of the PLGA breath figure technique for use in glaucoma drainage devices.

Figure 20:
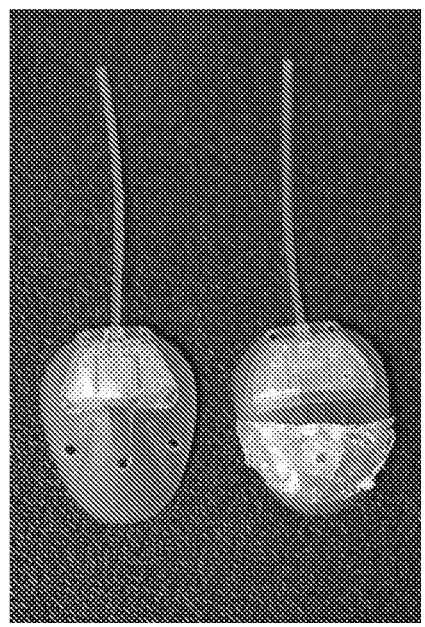
FIG. 20 shows a commercially purchased Ahmed Valve (left hand side) and a PLGA film coated valve with the "breath figure" structure (right hand side). The Ahmed valve is made of medical grade silicone.

MMC (sparingly water soluble) is a highly potent drug whereas 5-FU (highly water soluble) has much lower potency. MMC rapidly degrades in both acidic and basic conditions, and is also rapidly decomposed by elevated temperature and exposure to light. In contrast, 5-FU is a highly stable drug and is readily available. FIG. 20 is a photograph of commercially purchased glaucoma drainage device (GDD), the Ahmed glaucoma valve. The device on the left is an uncoated valve while that on the right is the valve coated with a breath figure PLGA film. The glaucoma device is made up of medical grade silicone and it incorporates a pressure sensitive, unidirectional valve that is designed to open when the intra-ocular pressure (IOP) is 8 mm Hg or greater. In the embodiment shown, we have used an 8 mm silicone disk (the material of the Ahmed valve) as the substrate over which the drug containing PLGA films are coated.

Figure 23:
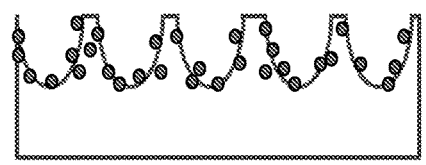
FIG. 23 illustrates a schematic of mitomycin C (MMC) loaded into pores at the top of an exemplary PLGA film.

The patterned microporous structure of the PLGA film provides a surface with the ability to bind and subsequently release pharmaceuticals, and preliminary studies were performed to evaluate these films for their ability to serve as reservoirs for the release of MMC. FIG. 23 illustrates schematically the placement of MMC on surface layers of the PLGA breath figure, while FIG. 24 is an electron micrograph of an exemplary breath figure structure, onto which MMC was loaded. This micrograph demonstrates that the surface PLGA layer retained its microporous structure even after MMC was loaded in a solvent mixture containing 5:1 methylene chloride/tetrahydrofuran. Because MMC can be inactivated under a wide range of conditions, these MMC-loaded discs were also tested for cytotoxicity. Silicone discs coated with PLGA alone or surface-loaded with varying concentrations of MMC (0.25, 1.0 and 5 μg) were tested for their ability to inhibit COS-1 proliferation during a 5-day culture period. The photograph in FIG. 25 shows cell accumulation in a 12-well plate and visually demonstrates that MMC is released from the polymer films and inhibits cell proliferation. In the absence of MMC, the control polymer (labeled C) permits growth of COS-1 cells to a confluent monolayer. Cells cultured in the presence of the control polymer showed the same degree of confluence as cells grown without a polymer sample. This suggests that the PLGA was biocompatible and nontoxic to COS-1 cells during the 5 day incubation period. As the concentration of MMC on the polymer films increased, cell accumulation in the plate decreased. These data are quantified in FIG. 26, which demonstrate that MMC inhibits cell proliferation in a dose-dependent manner. The observation that 1-5 μg MMC was sufficient to significantly inhibit cell growth to 40% or less of that in control cultures was of importance in designing the drug loading of the later PLGA composite films.

Figure 27:
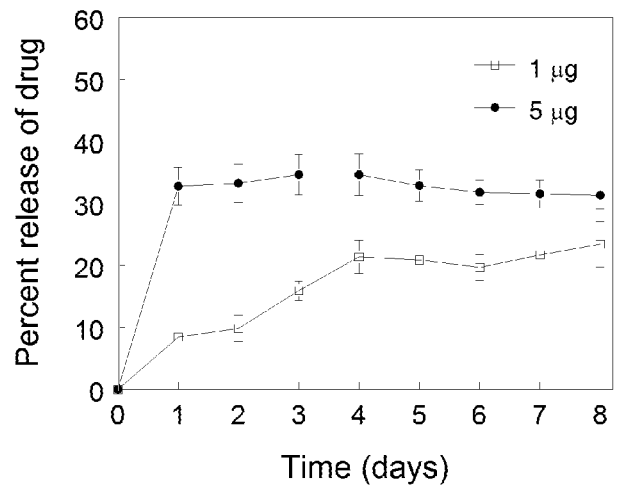
FIG. 27 shows the in vitro release profile for 1 µg and 5 µg MMC loadings.
Figure 28:
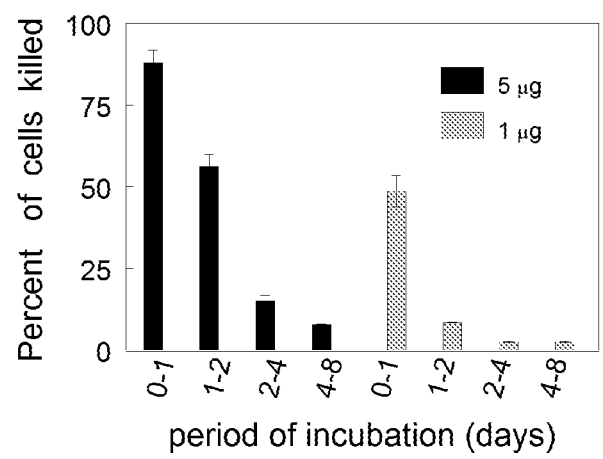
FIG. 28 shows the cytotoxicity of 1 µg and 5 µg MMC loadings released over an 8-day period.

The experiments shown in FIGS. 25 and 26 above do not provide any information about the kinetics of drug release, since they integrate the effect of MMC on growing cells over a 5-day culture period. The time-dependent release of MMC from these PLGA films into PBS is shown in FIG. 27 for films loaded with 1 and 5 μg MMC, the concentrations most active in inhibiting cell proliferation. Clearly, most of the MMC was released very early after immersion into the PBS; this burst of drug release can be attributed to rapid dissolution of surface-bound drug. Based on absorbance at 364 nm, which is characteristic of the active drug, it appears that only 20-40% of active drug is released from the film. This was not unexpected, based on the reported sensitivity of MMC to extremes of pH, light and temperature. The cytotoxicity of MMC released during timed incubation with cell culture medium provided release data similar to that for the in vitro release into PBS, as shown in FIG. 28. In these experiments, the drug released in culture medium at each indicated time interval was individually tested for cell toxicity. These experiments also showed a very rapid release of anti-proliferative activity from the PLGA surface, with most of the active drug release within 1 day. The decrease in cytotoxicity over subsequent time intervals indicated that the drug was virtually depleted after the initial burst. Remnant levels of the drug adsorbed to the polymer were responsible for the cytotoxicity effects observed after the first 1-2 days. As was observed in the in vitro release experiments, the $IC_{50}$ for the PLGA-bound drug was ~10 fold lower than that calculated for soluble MMC added directly to COS-1 cells.

Although the data in FIGS. 23-28 demonstrated that the anti-proliferative effect of MMC could be delivered from surface-loaded PLGA films, the drug release was too rapid to be effective for a glaucoma drainage device, since the fibroblasts that are responsible for the excess fibrosis around the GDD do not migrate into the surgical site until later in the wound healing process. Attempts to delay the release of MMC by incorporating it directly into the PLGA matrix were unsuccessful because the MMC was rapidly degraded under these conditions and the degradation products were not cytotoxic. Experiments were therefore initiated to formulate 5-fluorouracil (5-FU), a stable, water-soluble antifibrotic agent commonly used in ophthalmology, into slow release PLGA breath figure films.

Example 5A: Fabrication of Drug Loaded Double-Layered Breath Figure PLGA Films

Figure 29:
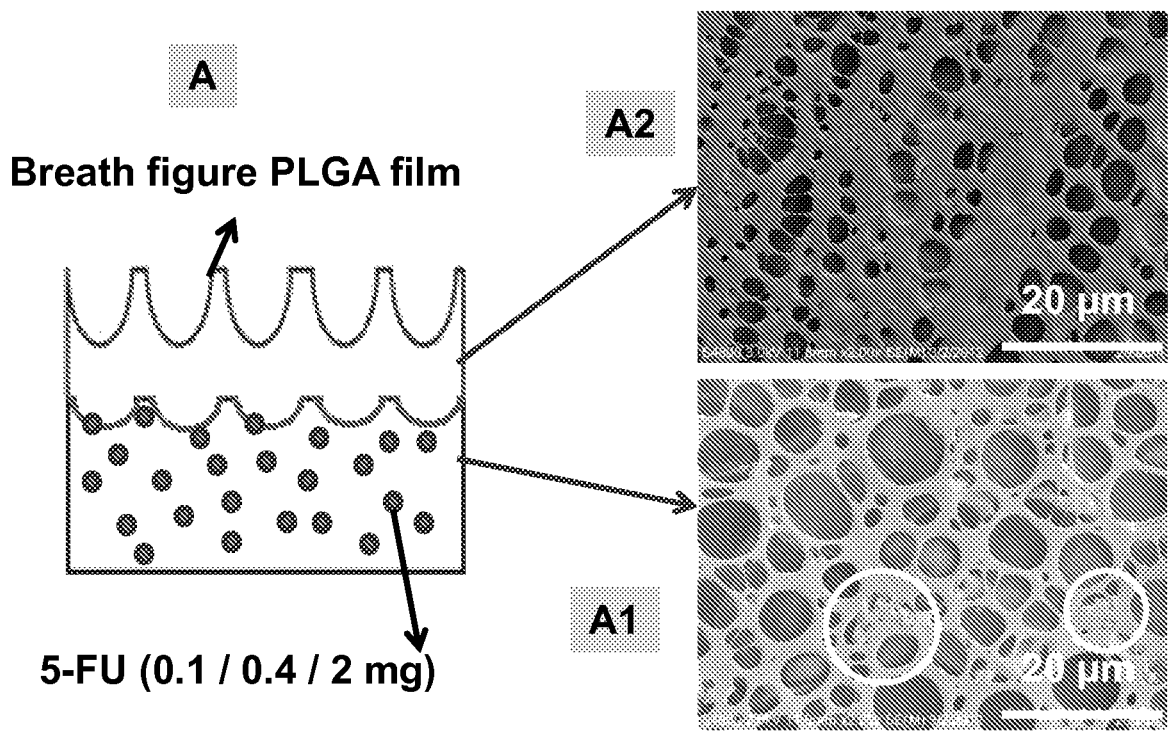
FIG. 29 is a schematic illustration of 5-FU incorporation into an exemplary double-layered breath figure PLGA film without MMC. Panel A shows 5-FU loadings into the bottom PLGA layer and the sealed breath figure PLGA film at the top (with no MMC). Panel A1 and A2 show the corresponding SEM images of the drug loaded bottom layer (before sealing) and the top sealed film.
Figure 30:
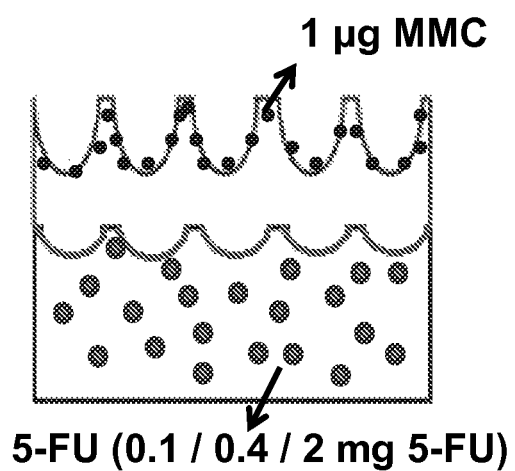
FIG. 30 is a schematic illustration of 5-FU incorporation into an exemplary double-layered breath figure PLGA film with MMC. The figure shows the 5-FU loadings into the bottom PLGA layer and 1 µg MMC loading on the top sealed layer.

In order to achieve prolonged cell growth inhibition, we fabricated double-layered breath figure PLGA films, containing 5-FU as the major anti-fibrotic agent. Two different exemplary systems were developed to achieve a continuous release of antifibrotic agent(s) over a period of ~1-30 days. The scheme of FIG. 29 shows the two layers of breath figure films fabricated one above the other. In that scheme, 5-FU was physically dispersed mainly into the bottom layer of a PLGA film and then sealed with another layer of thin film with no drug. SEM characterization (FIG. 29A1) reveals the porous structure in which the presence of 5-FU can be clearly observed (shown in circles). The representative electron micrograph corresponds to a film containing 0.4 mg 5-FU, before sealing the structure with another thin film. A second breath figure structure was created while coating the second layer (as shown in FIG. 29A2). To encapsulate the entire drug into the film, the bottom layer was spun at low speed, which resulted in a relatively thick drug-loaded bottom layer (~200 microns). The second layer was spin coated at higher speed to produce a very thin film (~20 microns). The creation of this second layer may disrupt to some extent the structure of the bottom layer, because the solvent used in the fabrication of the second layer could penetrate to the lower layer and modify its structure. The shallower surface morphology of the second layer in the schematics of FIGS. 29 and 30 reflects this possibility. Another scheme is shown in FIG. 30, with the difference being the surface coating of MMC. Like Scheme I (FIG. 29), these films were composed of a bottom layer containing 5-FU followed by a sealing layer. After the sealing, 1 µg of MMC was loaded on the surface while retaining the breath figure structure.

Figure 31:
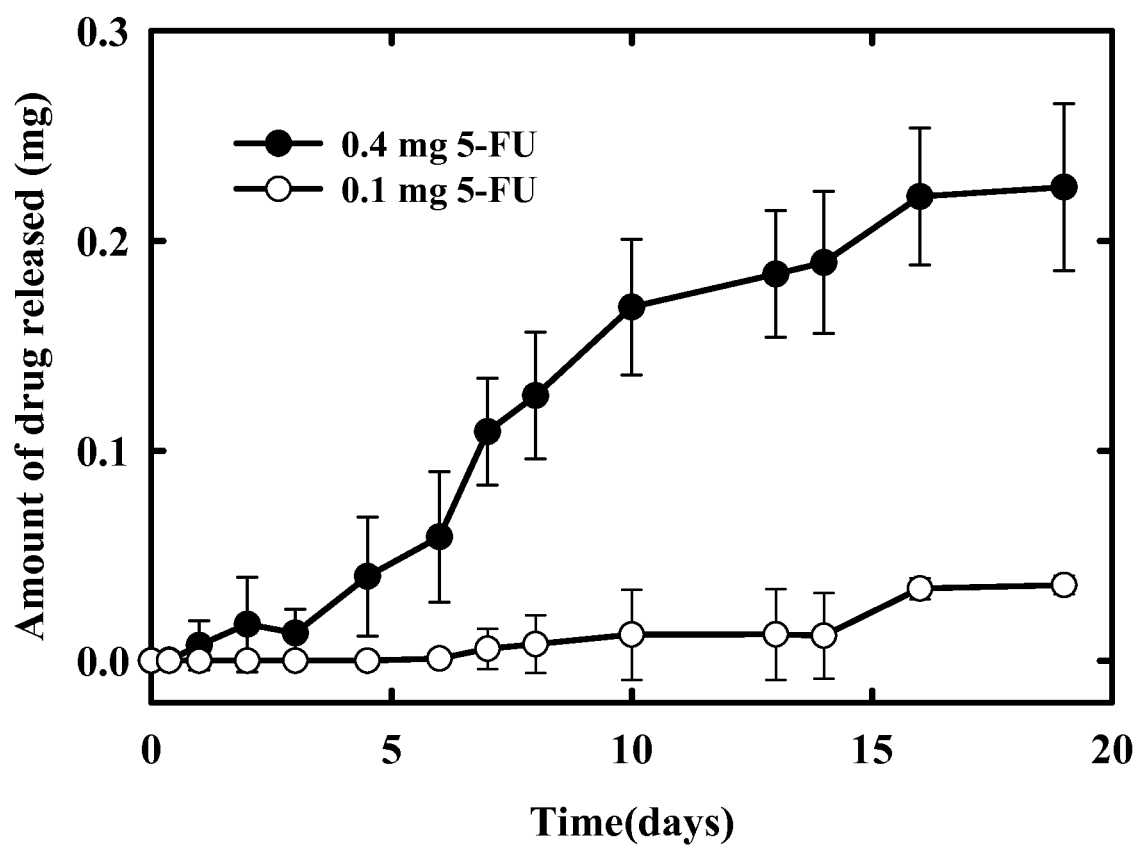
FIG. 31 shows in vitro release characteristics of 0.1 mg and 0.4 mg 5-FU from double layered breath figure PLGA films without a therapeutic loaded on the top layer. The delayed release can be observed due to the sealed top PLGA layer.
Figure 32:
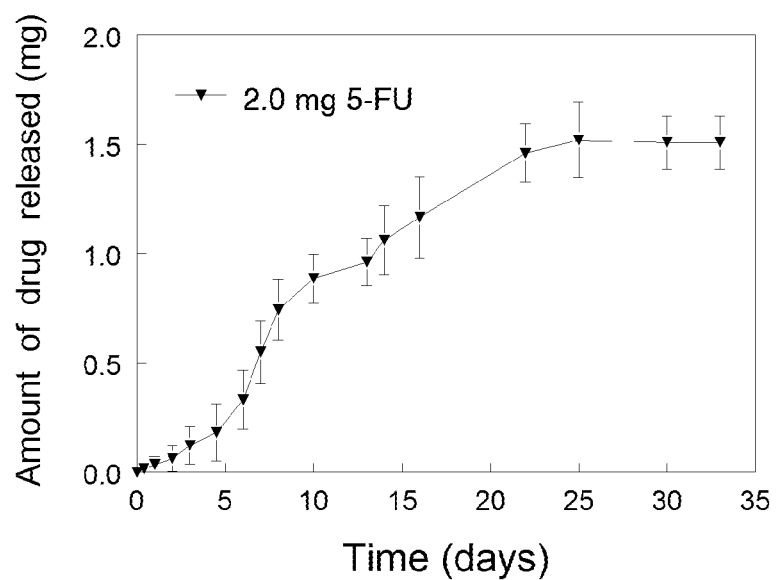
FIG. 32 shows in vitro release characteristics of 2 mg 5-FU from a double layered breath figure PLGA film without a therapeutic loaded on the top layer. The delayed release can be observed due to the sealed top PLGA layer.

Example 5B: In Vitro Release and Degradation Characteristics of 5-FU Loaded Films The in vitro release profiles of double-layered PLGA films containing 5-FU are shown in FIGS. 31 and 32. Because of differences in scale, release kinetics for films containing 0.1 and 0.4 mg of 5-FU are shown in FIG. 31, while the data for films containing 2 mg 5-FU are shown in FIG. 32. As expected, the release pattern showed no burst effect in the first 24 hours of incubation, indicating that the sealing procedure was fully effective. The sealing delayed the initial release of 5-FU for 3-5 days. Subsequently, there was a sharp increase in drug release that continued for 10 days. Following this phase, the release entered a shorter lag period that lasted 2-3 days. The initial delay in the drug release provided additional time for the degradation of the bottom layer of PLGA film containing 5-FU. The lag phase is followed by a continuous release of drug for 21 days. Virtually identical absorbance data was obtained for the second scheme (FIG. 30), because the small amounts of MMC surface-loaded onto these films was spectroscopically silent under the conditions used for these release experiments.

In previous studies, when drug moieties were incorporated into the single layered PLGA film (with no sealing), the drug release from the PLGA followed a tri-phasic profile. Immediate dissolution of surface bound drug resulted in a burst of drug release within 24 h. This was followed by an extensive lag phase during which the polymer was degraded with minor drug release. Once the polymer had been substantially degraded, the drug diffused out continuously with minor obstructions. In the examples presented here, it appeared that the top sealing layer modified release profiles to prevent the initial burst release. As the bottom layer drug-containing became exposed, the release that accompanied PLGA degradation occurred without a significant lag phase.

Figure 33:
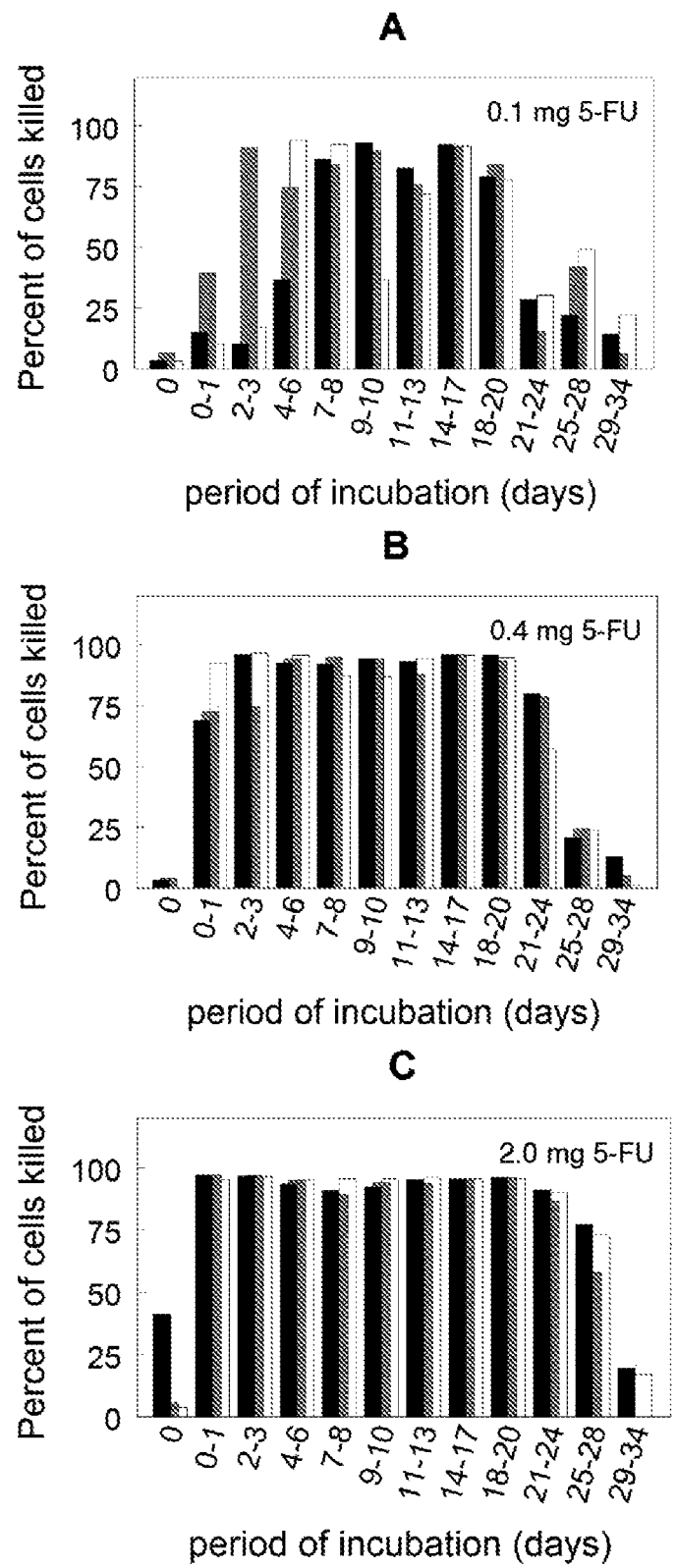
FIG. 33 shows in vitro cytotoxicity of 5-FU loaded double layered breath figure PLGA films from Example I. Panel A, B and C show the cytotoxicity for double-layered films containing only 0.1, 0.4 and 2 mg 5-FU, respectively. For 0.1 and 0.4 mg 5-FU, inconsistent toxic effect was observed for initial 5 days which is due to the sealed top layer with no drug content.

Example 5C: In Vitro Cytotoxicity of 5-FU Drug Loaded Double-Layered Breath Figure PLGA Films The sensitivity of COS-1 cells to drug released from the double-layered PLGA films fabricated using scheme 1 (FIG. 29) is shown in FIG. 33. The cytotoxicity of samples with 3 different levels of drug loading (0.1 mg, 0.4 mg and 2 mg 5-FU) was assessed. The cytotoxicity of drug released at different periods of incubation was quantified by culturing cells for 5 days, fixing/staining the cell monolayers with toluidine blue and measuring absorbance, as described above. The data was normalized to obtain the percent of cells killed as compared to a PLGA film without drug. FIG. 33A shows the results from the analysis of triplicate PLGA films containing 0.1 mg 5-FU. The graph shows variations in the toxicity among the three samples tested at early time points in the experiment. This heterogeneity was due to drug loading, film thickness and morphology. In addition, this cell-based cytotoxicity assay has a relatively narrow linear range, and low level of drug incorporated into these samples enhanced our ability to measure small differences in cytotoxicity among the triplicate samples. At longer time points in the experiment (samples from >15 days of incubation with culture medium), the triplicate samples demonstrated much less variation, with a killing efficiency of about 75%.

The triplicate samples that contained higher concentrations of 5-FU (0.4 and 2 mg) showed better reproducibility in the cytotoxicity assays, as shown in FIGS. 33B and C. In the samples loaded with 0.4 mg of 5-FU, maximum cytotoxicity was not attained until the samples had been incubated with culture medium for a total of 4-5 days. This delay in drug release was due to the sealing of the drug-bearing layer with a second thin PLGA film. In the polymer samples that contained 2 mg of 5-FU (FIG. 33C), the high quantity of drug in these polymer samples most likely exceeded the linear range of our cytotoxicity assay. The cytotoxic activity eluted from these samples remained high from day 1 and stayed constant until the PLGA layer was almost completely degraded (see FIGS. 35-36, see below). The effect of thin film sealing could not be observed in the assay in the presence of such a high drug dose.

Figure 34:
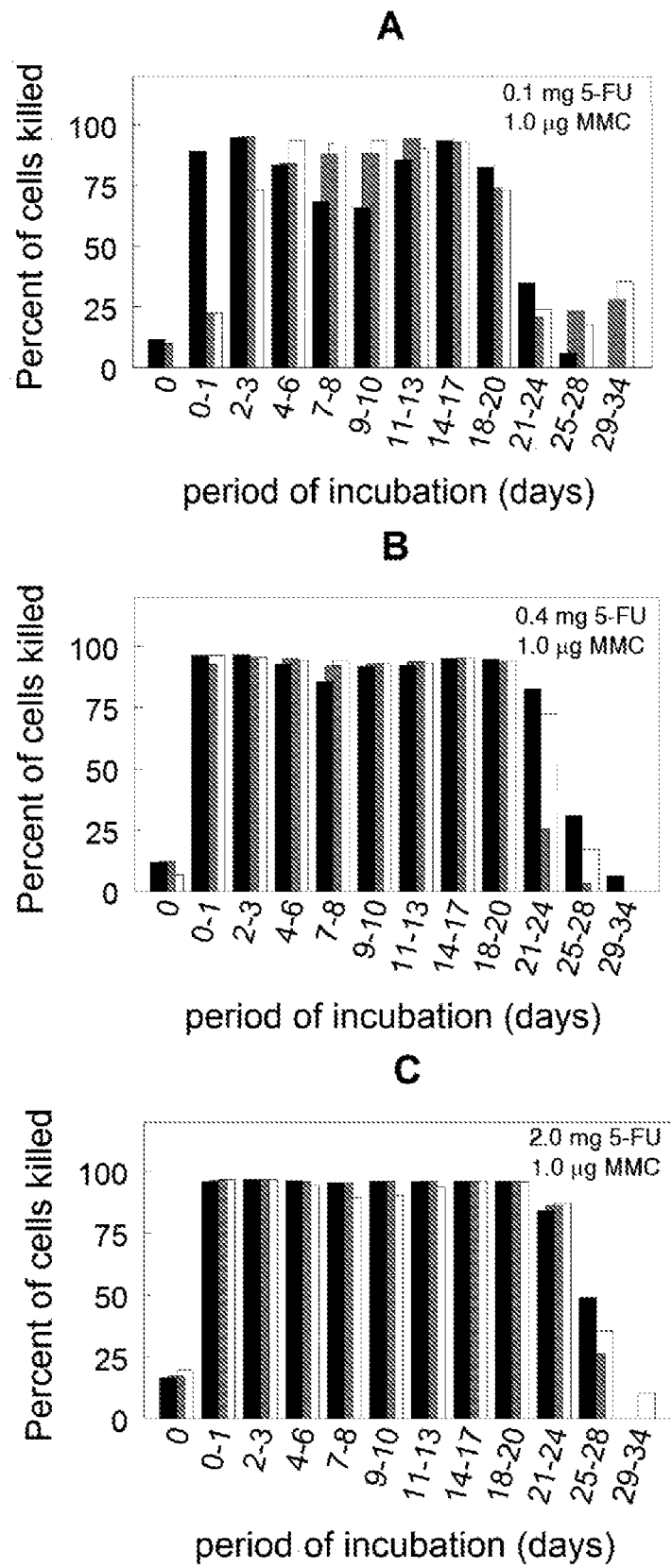
FIG. 34 shows in vitro cytotoxicity of 5-FU/double layered breath figure PLGA films from Example II. % of COS-1 cells killed are shown for a period of 34 days.

Example 5D: In Vitro Cytotoxicity of MMC/5-FU Drug Loaded Double-Layered Breath Figure PLGA Films We surface-loaded 1 µg MMC onto the top, sealing layer of our PLGA films and the cytotoxicity of drug eluted from formulations with three different loadings of 5-FU is shown in FIG. 34. For films containing 0.1 mg 5-FU loading (FIG. 34A), the cytotoxic effect of eluate from the PLGA films during the first 2-5 days became much less heterogeneous. This was due the burst release of surface-loaded MMC, which occurred before the later release of 5-FU. Similarly, in the case of 0.4 mg 5-FU, the effect of MMC is apparent, as shown in FIG. 34B. The inhibition of cell proliferation is profound throughout the experiment in the presence of moderate loading of 5-FU. It is clear that the initial toxicity effect (5 days) is due to the release of surface bound MMC and in the later stage, the release of 5-FU continues to control the cell proliferation. Thus, films prepared by this formulation have the ability to continuously deliver anti-fibrotic medication for up to 28 days.

Example 5E: Degradation Pattern of the 5-FU Loaded Double-Layered PLGA Films

The morphology of uncoated silicone and breath figure PLGA-coated samples was characterized using field emission scanning electron microscopy (Hitachi S-4800) as previously described (Ponnusamy T, Lawson L B, Freytag, L C et al. In vitro degradation and release characteristics of spin coated thin films of PLGA with a "breath figure" morphology. *Biomatter.* 2012; 2:77-86). All samples were coated with a thin layer of gold using a sputter coater (Polaron SEM coating system) prior to imaging. Both the pore dimensions and the thickness of coatings were examined. Samples containing 0.4 mg 5-FU were chosen for a study of the degradation pattern of double-layered 5-FU loaded PLGA films. These samples were incubated in 10 mL PBS (pH, 7.4) at 37° C. for periods up to 28 days. At weekly intervals, films were withdrawn, rinsed carefully with distilled water, and then air-dried prior to imaging.

Figure 35:
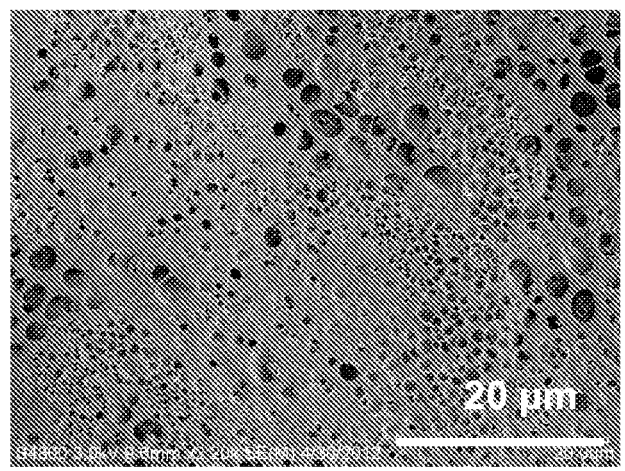
FIG. 35 shows the change in surface morphology of the degradation of 0.4 mg 5-FU loaded double-layered PLGA film incubated for a period of 28 days. Images were taken by SEM.
Figure 35:
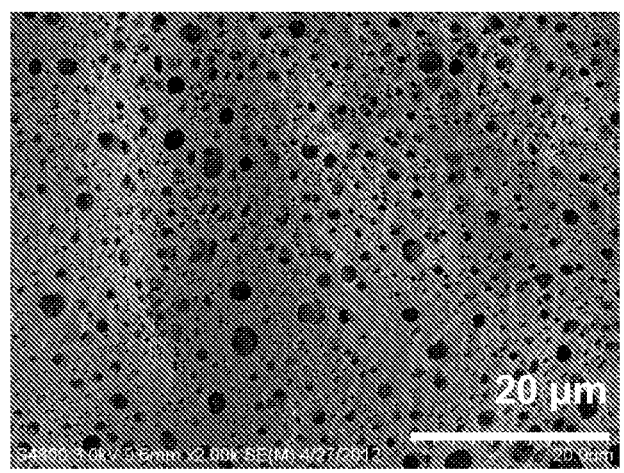
Figure 35:
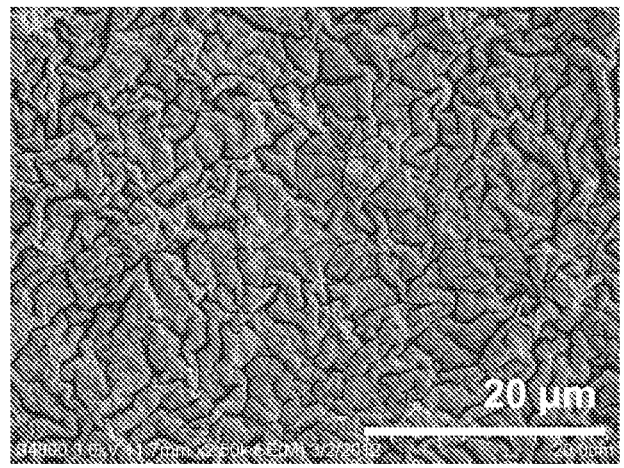
Figure 36:
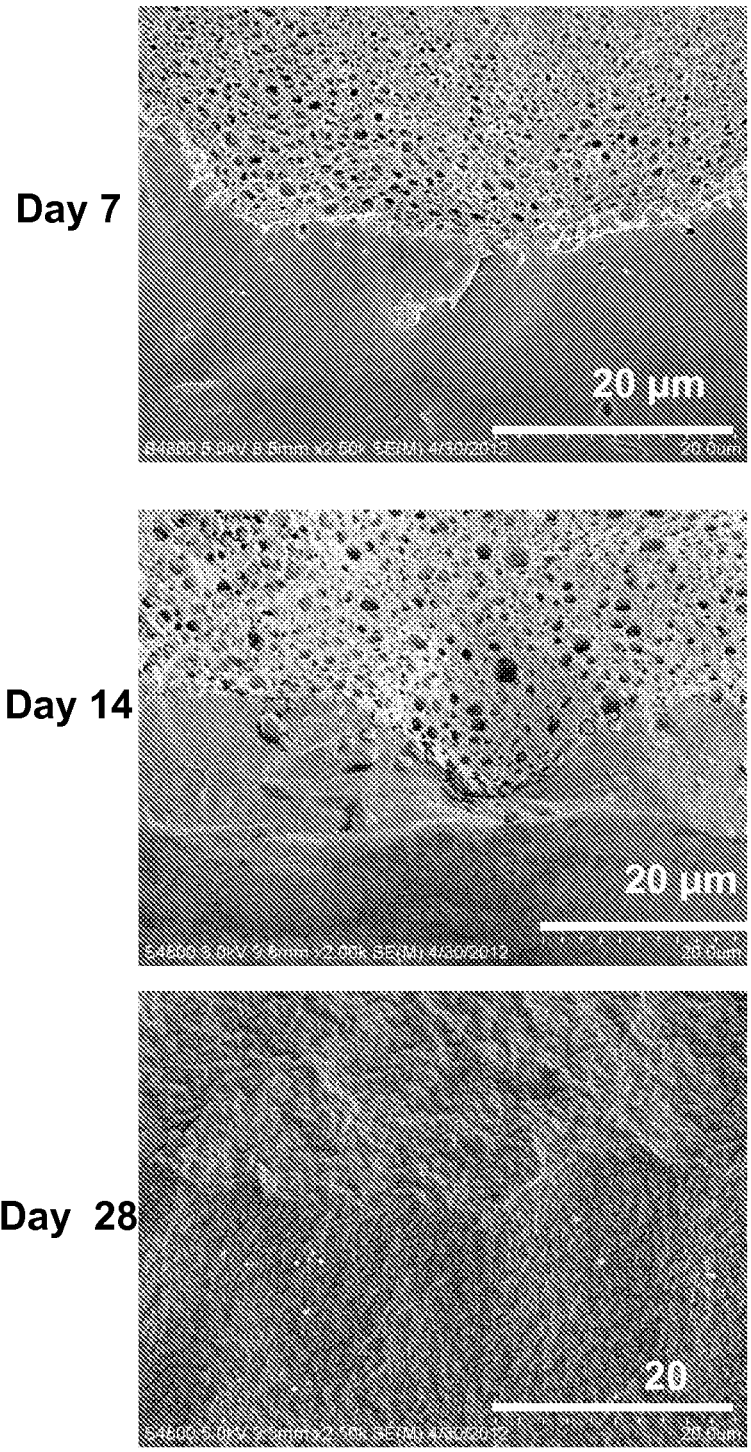
FIG. 36 shows the change in cross-section morphology of the degradation of 0.4 mg 5-FU loaded double-layered PLGA film incubated for a period of 28 days. Images were taken by SEM.

FIG. 35 (surface view of films) and FIG. 36 (cross-sectional view of films) illustrate the morphological analysis of the degradation of the double-layered PLGA film over a period of 28 days. The film contains 0.4 mg 5-FU in the bottom layer with a sealing top breath figure PLGA layer with no loaded drug. FIGS. 35 and 36 show the surface and cross-sectional view of the degradation, respectively. Within 7 days, the deterioration of irregular breath figure pores was clearly visible. From the side view (FIG. 36, day 7), the bottom layer had very little porous structure either in the bulk phase or in the thick dense layer of the film. With time (after 14 days) the film began to degrade and become permeable to aqueous medium. This generated irregular pores (pinprick pores) all over the film, which were not part of the original breath figure structure. The surface of the film also became slightly wrinkled due to the larger ingress of water, which can be observed from the side of view of day 14 degradation. After 28 days of incubation, the dense bottom layer was observed to be heavily swollen and wrinkled. We also observed that the polymer film stayed intact on the silicone substrate throughout the degradation process.

Example 5F: Dose Response Studies of Mitomycin C (MMC)

Figure 37:
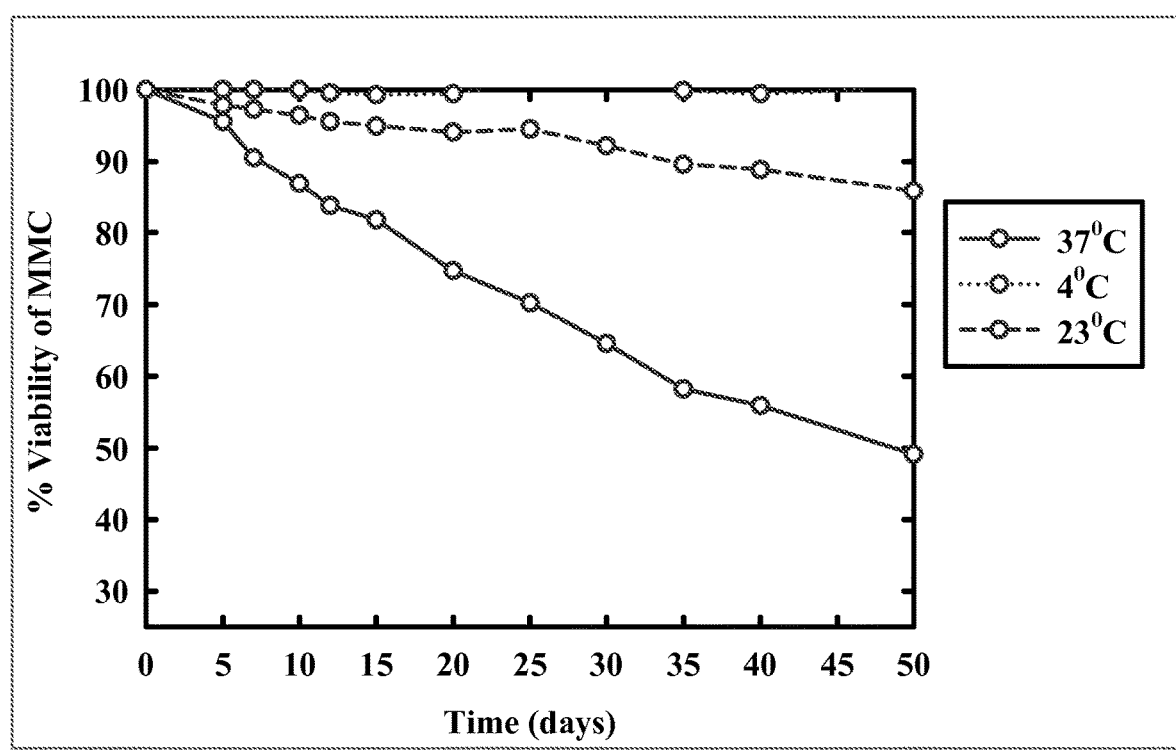
FIG. 37 illustrates the stability of MMC in PBS at different temperatures.

LOADING OF MMC ONTO THE SURFACE OF BREATH FIGURE PGLA FILM. Preliminary studies were performed to study the stability of MMC in both phosphate buffered saline, after surface loading onto PLGA breath figures and after dissolution in the PLGA-dichloromethane matrix and subsequent spin-casting. The stability of MMC in phosphate buffered saline is shown in FIG. 37. MMC retained its activity for 50 days at 4 degrees C. but lost approximately 15% of its activity at 23 degrees C. and 50% of its activity at 37 degrees C. during the 50 day incubation period. When dissolved into PLGA-dichloromethane and subjected to the spin-casting process, MMC lost 100% of its activity and PLGA films prepared in this manner had no more toxicity than control films without the therapeutic agent. Only the top-loading technique described herein retained the activity of MMC in the breath figure forma (see FIG. 26). To determine the optimum concentration of MMC, we sought to obtain the dose response of MMC using COS-1 cells. In the presence of humid air, 20 µl of PLGA solution (15% RG 504 w/v in methylene chloride), was loaded onto 3.5 mm silicone discs and spin coated (2500 rpm for 30 sec) to produce the breath figure PLGA films. After the films had dried, MMC was dissolved in a solvent mixture (5:1 v/v methylene chloride:tetrahydrofuran) and dropped uniformly onto the surface of breath figure PLGA films. After drying, the samples were UV sterilized for an hour prior to conducting studies of drug release and COS-1 sensitivity to the released drug. The cytotoxicity of PLGA films loaded with three different levels of MMC (0.25, 1.0 and 5 µg) were evaluated (described below). Control samples containing no MMC were prepared in an identical manner.

CELL CULTURE AND RELEASE STUDY. For the dose response study, control samples (no drug) and MMC-containing samples were loaded into sterile 12-well plates. For each column of a 12-well plate, triplicate samples were used, with the control, 0.25 µg, 1 µg and 5 µg MMC samples constituting each column. COS-1 cells ($10^4$ cells) were added to each well and the cells were incubated at 37° C. in a humidified 5% $CO_2$-95% air atmosphere. The culture medium was replenished on day 3 and day 5 after the cells were plated. After 5 days of culture, the cell accumulation in each culture dish was assessed. The culture medium was removed and the cell layer was gently washed 3 times with 5 mL of phosphate-buffered saline (PBS). The polymer piece was then removed from each well; cells were fixed for 30 minutes in 5 mL of neutral buffered formalin, then stained for 1 hour with 5 mL of 1% toluidine blue in neutral buffered formalin. The dye solution was removed, the cell layer was washed 4 times with 5 mL of distilled water, and the plate was allowed to air-dry overnight at room temperature. Dye bound to the fixed cells was solubilized by the addition of 2 mL of 2% aqueous sodium dodecyl sulfate (SDS), followed by incubation for 15 minutes. The amount of dye in each well was measured by the absorbance at 650 nm, which is equivalent to the number of cells, using UV-Visible spectrophotometer (Model UB-1601, Shimadzu scientific instruments Inc, Houston, Tex.).

Release studies on films loaded with 1 µg and 5 µg MMC were performed in glass vials containing 1 mL PBS as the release medium. This experiment was not performed for polymer samples containing 0.25 µg MMC, due to the difficulty in quantifying UV absorbance at this low drug concentration. Aliquots (0.65 mL) of the PBS were removed at specific time intervals after immersion of the polymer samples, and absorbance was measured at 364 nm using a UV spectrophotometer (Shimadzu UV-1700 series). After measurement, the aliquots were returned to the vials to maintain constant volume and sink conditions. The concentration of drug release was calculated from a linear calibration curve plotted from known concentrations of MMC.

CYTOTOXICITY OF DRUG RELEASED OVER A 5-DAY PERIOD. For the preliminary dose-response study, COS-1 cells ($10^4$ cells in 1 mL) were added to each well of a 12-well plate. The cells were allowed to adhere on the tissue cultures plates for 4 h at 37° C. in a humidified 5% $CO_2$/95% air atmosphere, then an additional 2.5 mL of culture medium was added. Transwell inserts, each containing a sample of drug-loaded polymer (n=3 for each sample type), were then placed on top of the wells in the 12 well plates, so that each polymer piece was submerged in the culture medium. The cells were cultured for 5 days without a change of medium. During this time period, the drug incorporated into the polymer was released into the culture medium. After 5 days of culture, the cell accumulation in each culture dish was assessed by a modification of a previously described procedure (Leavesley D I, Ferguson G D, Wayner E A, et al. Requirement of the integrin beta 3 subunit for carcinoma cell spreading or migration on vitronectin and fibrinogen. J Cell Biol. 1992; 117:1101-1107.) Briefly, culture medium was removed and the cell layer was gently washed 2 times with 2 mL of phosphate-buffered saline (PBS). Cells were fixed for 1 hr in 0.5 mL of neutral buffered formalin, then stained for 1 hour with 0.5 mL of 1% toluidine blue in neutral buffered formalin. The dye solution was removed, the cell layer was washed 4 times with 2 mL of distilled water, and the plate was allowed to air-dry overnight at room temperature. All plates were scanned to make a photographic record, and the incorporated dye was subsequently dissolved by adding 0.5 ml 2% SDS to each well and rocking the plate for 1 h at 25° C. Aliquots (3×100 µL) of the dissolved dye were read at 650 nm with a 96-well plate reader (VersaMax, Sunnyvale, Calif.).

Example 5G: Fabrication and In Vitro Cytotoxicity of 5-FU (Scheme I) and 5-FU+ MMC (Scheme II) Loaded Using Double-Layered PLGA Films We found the incorporation of small amount of MMC into the bulk PLGA film results into drug degradation and the degraded products showed no toxic effect on COS-1 cells. In order to obtain prolonged release, we chose a highly stable 5-FU drug in the formulation. Using 5-FU as the major anti-fibrotic agent, we fabricated two different delivery systems, namely 5-FU (formulation I) and 5-FU+MMC (formulation II) loaded PLGA films. Both the formulation systems consist of two layers of spin coated breath figure PLGA films one above the other.

5-FU LOADED BREATH FIGURE PLGA. The 5-FU drug particles were ground into a fine powder using a mortar and pestle set. The appropriate weight of finely ground drug was then dispersed into the PLGA solution (12.5% RG 506 w/v in methylene chloride) using bath sonication for 10 minutes. This resulted in a homogeneous "milky" polymer-drug solution. Under humid conditions, 75 µL of the polymer-drug solution was spun onto a washed 8 mm silicone disc for ~6 minutes at 200 rpm. This low speed spin insured that all of the polymer solution remained on the substrate. Three different loadings of 5-FU samples were prepared (0.1, 0.4 and 2 mg per 8 mm disc). The samples were dried for a day before fabricating a second layer. To coat a second layer, 50 µL of RG 504 PLGA (15% w/v in methylene chloride) was spin coated at 1000 rpm for 25 s. This process created a very thin film with the average thickness of 20 microns and was intended to be a seal over the first layer. All samples were UV-sterilized before studies of in vitro release, cell cytotoxicity and polymer degradation.

5-FU+MMC—BREATH FIGURE PLGA. In this embodiment, double-layered films were fabricated as described for Scheme I, then MMC was surface-loaded into the top layer. Based on preliminary dose response results, 1 µg of MMC was chosen for Scheme II. After fabrication of the double-layered films, 1 µg MMC in solution (5:1 v/v methylene chloride:tetrahydrofuran) was dispersed on the PLGA surface while reproducing the breath figure in a manner very similar to that used in the preliminary studies described above. To compare the effect of added MMC, three different loadings of 5-FU (0.1, 0.4 and 2 mg per 8 mm disc) were prepared, each with 1 µg of MMC surface loaded on the top of the PLGA film.

IN VITRO RELEASE CHARACTERISTICS OF DOUBLE-LAYERED 5-FU-PLGA FILM. In these experiments, 8 mm discs containing 5-FU incorporated films were incubated in 10 mL of PBS at 37° C. At specific time intervals, a 1 ml aliquot of the solution was withdrawn and 1 ml of fresh PBS was added to the vial to maintain constant volume. The pH of the medium was monitored during the course of the experiment to verify that the solution was buffered adequately during polymer degradation. Each aliquot was centrifuged to remove any possible debris from the degraded polymer components that could interfere with the absorbance readings and drug release was quantified through the absorbance measured at 266 nm. A standard calibration plot of 5-FU absorbance was constructed to correlate absorbance with drug release levels. All experiments were conducted with triplicate polymer samples.

IN VITRO DEGRADATION OF 5-FU LOADED BREATH FIGURE PLGA FILMS. To understand the degradation pattern of 5-FU loaded breath figure PLGA films, we chose films containing 0.4 mg 5-FU. The samples were incubated in 10 mL PBS (pH, 7.4) at 37° C. for a period of 28 days. At weekly intervals, the films were withdrawn and rinsed carefully with distilled water. The dried samples were analyzed by SEM to obtain the degradation pattern.

CYTOTOXICITY OF DRUG RELEASED OVER LONGER TIME PERIODS. Polymer samples with incorporated drug were placed individually into tubes containing 2 ml of DMEM without serum or other supplements and incubated at 37° C. in a humidified atmosphere of 5% $CO_2$/95% air. The entire medium sample was collected at a given time period interval and fresh medium (2 mL) was added to the polymer in the tube for the next incubation period. After incubation, the medium samples were stored in at 4° C. refrigerator until cytotoxicity testing. For the zero time incubation point, each polymer was briefly dipped into 2 mL of culture medium and transferred immediately into another tube for subsequent incubation. The sample collection intervals were every 2-3 days; incubation time periods were shorter in the early days and longer after 20-25 days. For early dose-response experiments with films surface-loaded with MMC, the total incubation time was 8 days (192 h). For double-layered films, the total time that each polymer sample was incubated sequentially with culture medium was usually 34 days. After ~20 days of incubation, the culture medium became acidic due to breakdown of the PLGA matrix. A small aliquot of sodium hydroxide was added to these samples to adjust the pH to 7.4 before cytotoxicity testing. When such neutralization was necessary, a similar polymer sample with no incorporated drug was used as a control to insure that any toxicity observed was due to the drug and not to changes in osmolarity because of the neutralization process.

All samples were tested after the entire 34 day incubation period had been completed. The 2 mL aliquot of DMEM that had been incubated with the polymer was mixed with 0.5 ml of culture medium supplemented with 50% FBS, 20 mM glutamine, 5 mM sodium pyruvate, 500 IU penicillin, 500 µg/mL streptomycin and 125 µg/mL amphotericin B such that the final 2.5 mL sample mixture had the same composition as complete culture medium. COS-1 cells were plated into 12 well culture plates at $1 \times 10^4$ cells per well by adding 1 mL of cell suspension to each well. The cells were allowed to attach for 4 hours, as described above, then the 2.5 mL of DMEM that had been incubated with the polymer sample was added to each well. The final volume of culture medium in each well was 3.5 mL. The cells were incubated for 5 days with no medium change and cell accumulation was assessed as described above.

Example 6: Model Study—Fenofibrate Containing PGLA Wafers for Use in Cancer Therapy

MATERIALS AND METHODS

CELL CULTURE. Human glioblastoma cell line LN-229 (ATCC #CRL-2611) monolayer cultures were maintained in DMEM supplemented with 50 U/ml penicillin, 50 ng/ml streptomycin, and 10% fetal bovine serum (FBS) at 37° C. and 5% $CO_2$ atmosphere. For HPLC analyses, the cells were seeded in 100 mm cell culture dishes and cultured in the presence of 10% FBS supplemented with fenofibrate, (at final concentration of 50 µM in DMSO). The medium and cellular samples were collected after 6, 10, 24, 48 and 72 h incubation. Membrane and cytosolic fractions were prepared from the control (DMSO) and fenofibrate treated LN-229 cultures by detergent-free subcellular fractionation based on hypotonic sucrose buffer and ultracentrifugation according to the subcellular fractionation protocol (Abcam, UK).

ANIMAL STUDIES. Immunodeficient Balb c/nude mice bearing intracranial human glioblastoma (LN-229) were treated with fenofibrate (50 mg/kg/day) administered by the oral gavage. Following 10 days of daily drug administration the animals were euthanized according to the standard ethically accepted procedure, and the following organs/body fluids were collected: blood, urine, liver, kidneys, spleen, heart, lungs, intact brain and intracranial tumor tissue. These tissues were subjected to sample preparation for the HPLC analysis for the detection of fenofibrate (FF) and fenofibric acid (FA) content. FA and FF calibration curves were applied to quantify the data. All experiments were performed according to the Guide for the Care and Use of Laboratory Animals and local bioethical committee procedures at LSUHSC (approval no IACUC #2902).

SAMPLE PREPARATION. Blood plasma, cell culture media, cellular and tissue lysates, were deproteinized by adding 150 µl of acetonitrile to 150 µl of sample, mixed well and centrifuged (15 000 g, 5 min). Urine and other samples that did not contain protein were centrifuged as above. For the subcellular fractionation, subconfluent monolayer cultures were washed in phosphate buffered saline (PBS) twice, then cells were scraped and lysed in 2% sodium dodecyl sulphate (SDS) in PBS. The lysates were sonicated on ice and centrifuged (15 000 g, 5 min). Finally, 150 µl of the supernatant was mixed with the equal volume of acetonitrile, filtered through 0.22 µm centrifuge filter (Sigma) and analyzed by High Performance Liquid Chromatography (HPLC).

HIGH PERFORMANCE LIQUID CHROMATOGRAPHY. All data were obtained from the Agilent Technologies 1100 apparatus equipped with a line degasser, binary pump (high pressure mixer), autosampler, column thermostat and Diode Array Detector (DAD). The YMCBase, 3 µm 4.6×150 mm analytical column was used and solvent A—50 mM acetic acid in water or solvent B—acetonitrile, with isocratic flow 60%. Flow rate was set to 1 ml/min, column temperature was 20° C., and 5 µl of 0.22 µm filtered sample was injected. DAD wavelength was set to 285 nm.

WESTERN BLOT. The purity of the cytosolic and membrane fractions prepared from the LN-229 cell lysates was checked by the detection of protein markers characteristic for these fractions, namely N-cadherin (rabbit monoclonal antibody from Cell Signaling Technology, USA) for the membrane fraction and glyceraldehyde-3-phosphate dehydrogenase (GAPDH, mouse monoclonal antibody from Fitzgerald Industries, USA) for the cytosolic fraction. Sample preparation and immunoblotting were performed according to standard procedures described in our previous publications (Wilk A, Urbanska K, Grabacka M, Mullinax J, Marcinkiewicz C, Impastato D, et al. Fenofibrate-induced nuclear translocation of FoxO3A triggers Bim-mediated apoptosis in glioblastoma cells in vitro. Cell Cycle 2012; 11:2660-71.).

Figure 38:
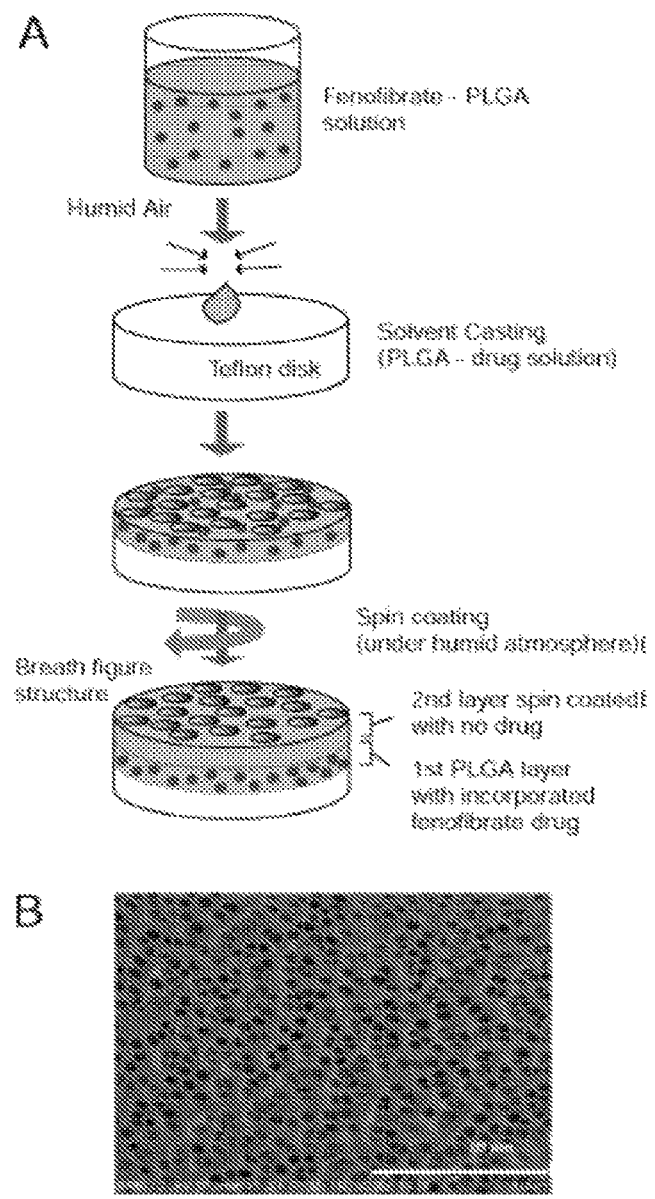
FIG. 38 is a schematic description of an embodiment of the preparation of PGLA wafers containing Fenofibrate ("FF") and an SEM image of a PGLA wafer prepared by the illustrated method.

PREPARATION OF PGLA WAFERS CONTAINING FENOFIBRATE. FIG. 38 is a schematic representation of the preparation of PGLA wafers according to this example. The fabrication consisted of two-layered porous biodegradable PLGA films, as describe above. See also: Ponnusamy T, Lawson L B, Freytag L C, Blake D A, Ayyala R S, John V T, "In vitro degradation and release characteristics of spin coated thin films of PLGA with a "breath figure" morphology". Biomatter 2012; 2:77-86; and Ponnusamy T, Yu H, John V, Ayyala R, Blake D., "A novel anti-proliferative drug coating for glaucoma drainages devices". J Glaucoma 2013; in press:doi: 10.1097/IJG.0b013e318294869b, both of which are herein incorporated by reference in their entirety. In these wafers, fenofibrate was incorporated into the bottom layer and sealed with a second PLGA layer without drug, as shown in FIG. 38A. The bottom layer was solvent cast and the sealing layer was prepared by spin coating. An 8 mm circular piece of teflon, used as the substrate, was rinsed with 95% ethanol to remove any surface contaminants. To prepare the coating solution, 1.3% (w/v) of fenofibrate was first dissolved in methylene chloride followed by dissolving 12.5% (w/v) of the PLGA (Resomer RG 506) polymer. The solution was vortex-mixed to ensure homogeneity. The appropriate volume (75 µL) of the solution containing PLGA and the drug (~107 mg drug/g polymer) was solvent cast onto the teflon at room temperature. Constant humidity was maintained (~50-60% relative humidity) while the solvent was slowly evaporated to produce a breath figure pattern on the film. The breath figure technique is a facile method of producing regular pores in a polymer film. The drug-loaded film was dried for a day before fabricating the second layer. The dried thickness of the film was measured to be ~150 microns. To coat a second layer, 50 µL of 15% (w/v) (Resomer RG 504) PLGA solution was spin coated at 1000 rpm for 25 s. This created a very thin film with an average thickness of 20 microns that was intended to be a seal over the first layer. Again, the second layer was cast in ~50-60% relative humidity to create pores on the top layer (surface scanning electron microphotography is shown in FIG. 38B). All fabricated samples were UV-sterilized for an hour and stored until cell clonogenic assays.

CHLONOGENIC ASSAY. LN-229 cells were plated at the clonal density ($1 \times 10^3$ cells per 35 mm dish) in the regular growth medium. The cells were exposed to the investigated compounds (fenofibrate, gemfibrozil, Wy-14,643 and metformin; all used at 50 µM) or to 1 mg of fenofibrate incorporated in the PLGA wafer during the 12 days of incubation. Control cells were treated with the vehicle (DMSO). At the end of each experiment, the cells were fixed and stained in the 0.25% crystal violet solution on methanol, air dried and the colonies were counted. All the conditions were tested in duplicate and each experiment was performed at least three times.

Results

Figure 39:
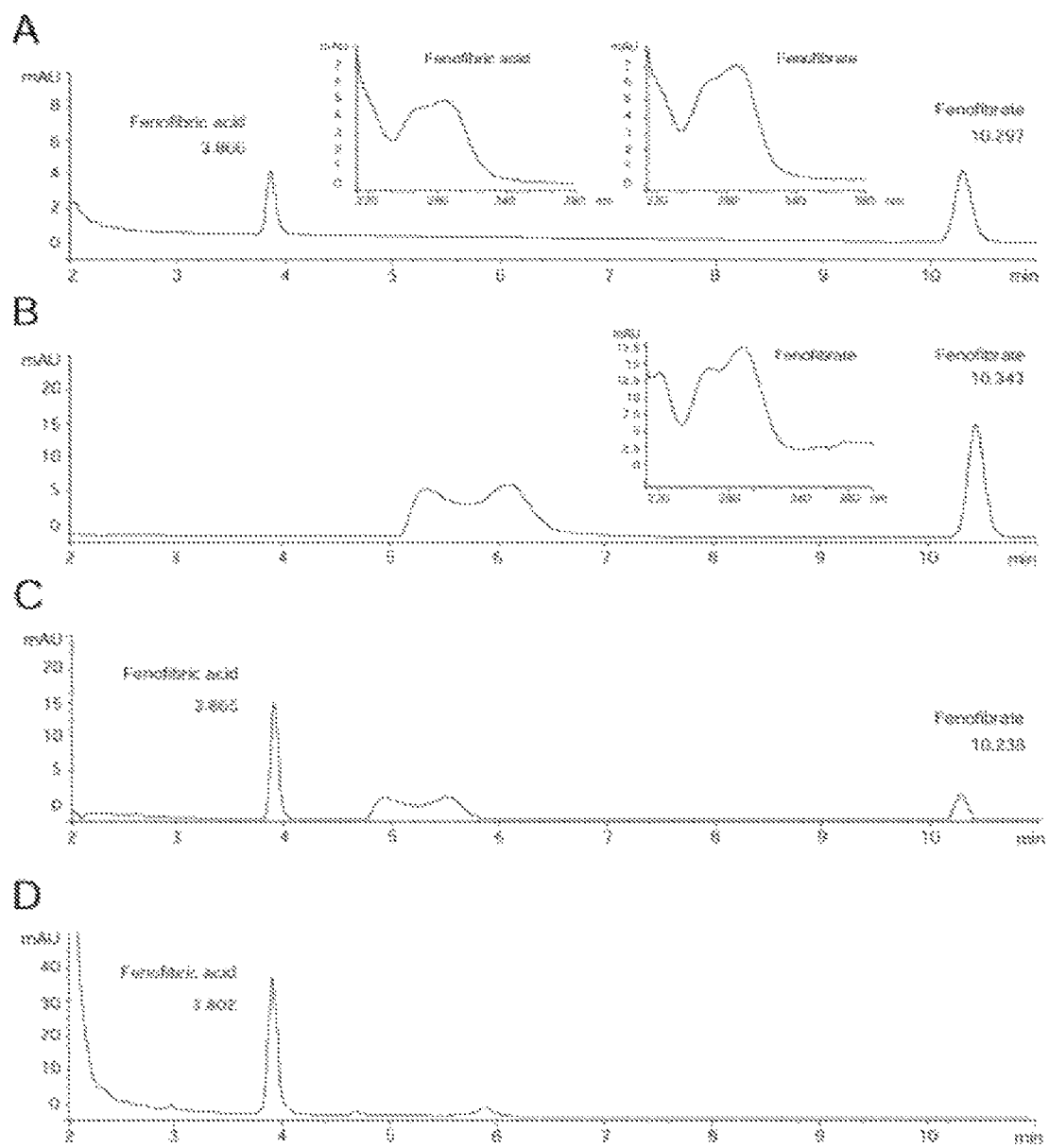
FIG. 39 are graphs produced by HPLC detection of FF and Fenofibric Acid ("FA").

JUSTIFICATION FOR THE HPLC DETECTION OF FENOFIBRATE AND FENOFIBRIC ACID IN BIOLOGICAL FLUIDS. FIG. 39 illustrates detection of FF and FA by high performance liquid chromatography [HPLC; Agilent Technologies 1100 with on line degasser, binary pump, auto-sampler, YMBCBase 3 µm, 4.6×150 mm column, thermostat, and diode array detector (DAD)]. The sample separation parameters were as follows: solvent a: 50 mM acetic acid in water; solvent b: acetonitrile, isocratic 60%; flow rate 1 ml/min; temp 20° C.; injection fraction 5 µl; detection: DAD at 285 nm. Panel A provides an HPLC chromatogram of FF and FA standards; Panel B provides FF 50 µM solution in human blood just after mixing (time 0); Panel C provides the same solution as in B after 4 hr incubation at 37° C.; Panel D provides an HPLC analysis of urine from the patient who takes fenofibrate regularly (200 mg of micronized fenofibrate daily). Insets: UV-Vis absorption spectra for FF and FA showing absorption maxima at 285 nm.

Hydrophobic properties and absence of pH dependent charged groups make fenofibrate easy to analyze with the reverse phase high performance liquid chromatography (HPLC) with various mobile phases. The low pH mobile phase was chosen to measure both fenofibrate (FF) and its PPARα active metabolite fenofibric acid (FA), because de-esterification (isopropyl group removal) results in the generation of FA. In such conditions acidic compounds are not charged, but FA is more polar than FF, and FA retention time in the HPLC column is therefore significantly shorter than FF. In the presented conditions the retention time for standard FF was 10.3 minutes and for FA 3.9 minutes (FIG. 39A). Due to the presence of aromatic rings in the structure, both FF and FA absorb light in UV range with very similar molar extinction coefficients. Indeed, the FF and FA absorption spectra are very similar with maximum absorbance at 285 nm (see corresponding insets in FIG. 39). The FF and FA detection method was initially tested using three types of samples: (i) 1 ml of human blood+1 ml of 50 µM FF in DMSO at time zero (T0; FIG. 39B); (ii) the same blood/FF mixture after 4 hrs incubation at 37° C. (FIG. 39C); and (iii) urine samples collected from individuals who take oral fenofibrate on regular basis (200 mg micronized fenofibrate daily) (FIG. 39D). In the freshly prepared mixture containing FF and human blood (T0), HPLC-based analysis detected a distinct peak characterized by the retention time and absorption spectrum identical to the standard FF, and the absence of FA (compare FIGS. 39A and 39B). Following 4 hours of FF exposure to the human blood, FF peak decreased about 5-fold at expense of a new peak whose retention time and absorption spectrum corresponded to FA standard (compare FIGS. 39A and 39C).

The decreased FF peak and appearance of FA is evidence for enzymatic processing of FF to FA by blood esterases, the most likely arylesterases, since standard FF solution is stable in culture medium for at least 120 h (longer times have not been tested). In agreement with the quick and effective enzymatic conversion of FF to FA in the blood and tissues, we did not detect any traces of FF in the urine samples (FIG. 39D), further confirming that all orally administered FF is metabolized and excreted as FA.

Figure 40:
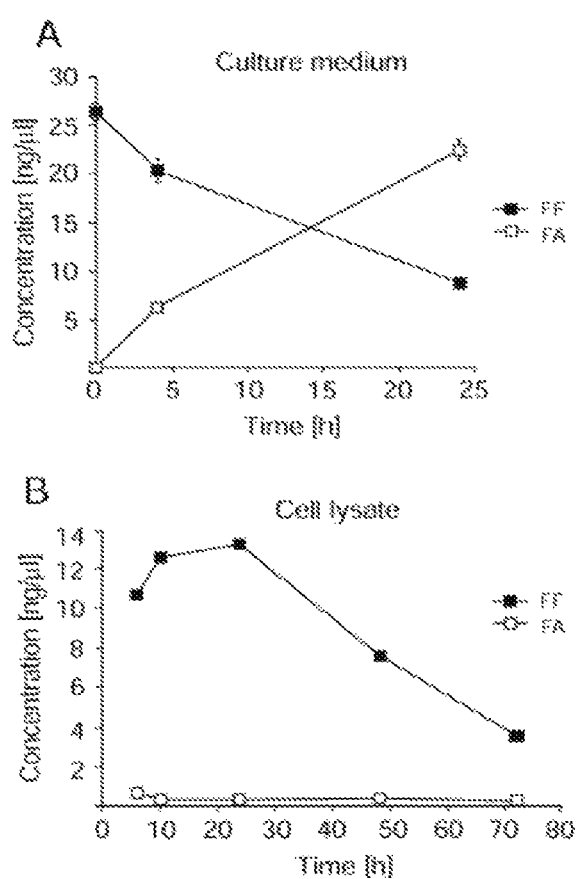
FIG. 40 is a graph showing results of an HPLC-based analysis of the time course of FF to FA exchange between cells and culture media.

FENOFIBRATE PHARMACOKNETICS IN CELL CULTURE. Our cell culture experiments have demonstrated that LN-229 human glioblastoma cells absorb FF from culture medium, and that intracellular esterases (the most likely carboxylesterases or arylesterases) metabolize FF to FA, which subsequently accumulates in the medium. FIG. 40 is an HPLC-based analysis of fenofibrate (FF) and fenofibric acid (FA) concentrations in cell culture media (A) and whole cell lysates (B) from the monolayer culture of human glioblastoma cell line, LN-229, treated with a single dose of fenofibrate (50 µM) determined at the indicated time points. HPLC parameters are given in the materials and methods section and in the legend to FIG. 39. Data represent average values from 2 experiments in triplicate (n=6)±SD (SD values for some points are too small to be visible). The results in FIG. 40 show the time course of FF to FA exchange between cells and culture media. In cells exposed to 50 µM FF, the drug accumulates quickly inside the cells reaching the maximal concentration at 24 hr, and then its concentration gradually decreases (FIG. 40A). In contrast, FA intracellular levels are much lower and constant during the course of experiment (FIG. 40B). In the medium, FA levels continuously increase, which together with the observed low intracellular FA levels, indicate that FA is continuously produced inside the cells and is released to the medium. However, it is also possible that FF may be processed to FA outside the cell by secreted esterases. To test this alternative interpretation, we collected conditioned medium from the LN-229 cells cultured for 72 hrs. This conditioned medium was filtered (0.22 µm pore size filter), and 50 ěM FF standard was added for 24 hrs at 37° C. Since we did not detect any traces of FA after this procedure (data not shown), we concluded that the filtered conditioned medium had no esterase activity and all FA detected in FIG. 40B was most likely released from the cells treated with FF.

Figure 41:
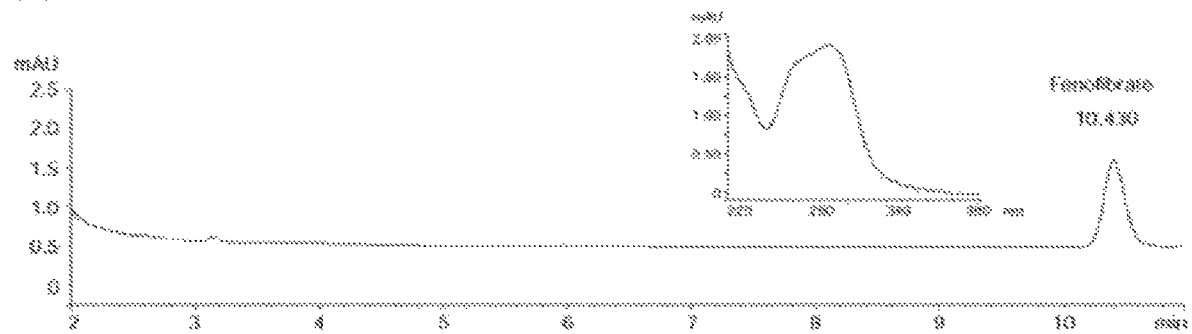
FIG. 41 illustrates HPLC-based detection of FF and FA in cystolic and cell membrane fractions isolated from FF treated human blioblastoma cell line, LN-229.
Figure 41:
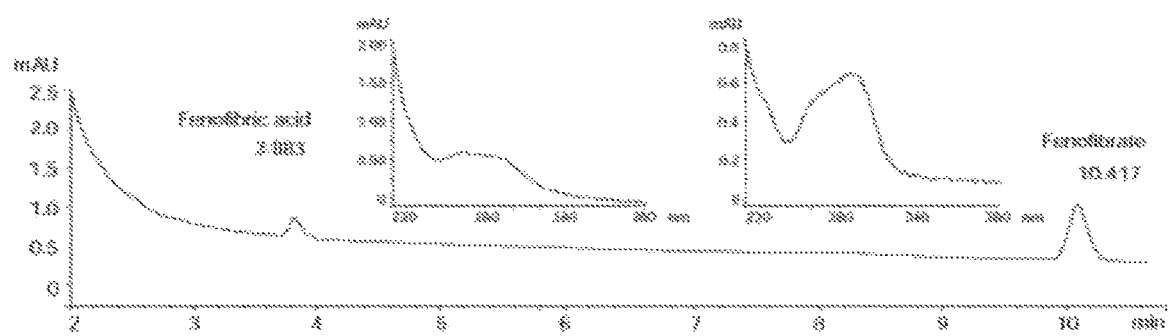
Figure 41:
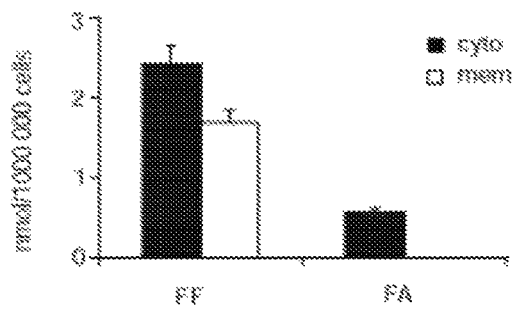
Figure 41:
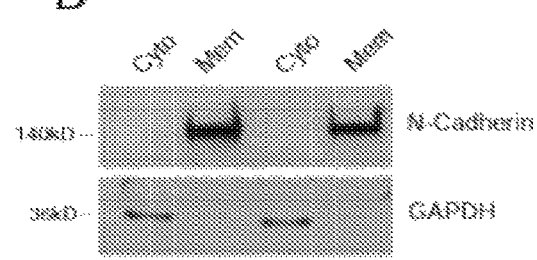

SUBCELLULAR DISTRIBUTION OF FENOFIBRATE. FIG. 41 is HPLC-based detection of fenofibrate and its metabolite, fenofibric acid, in cytosolic (Panel A) and cell membrane fraction (Panel B) isolated from fenofibrate treated human glioblastoma cell line, LN-229. Under this condition (see legend to FIG. 39), fenofibrate was eluted at 10.4 minutes and fenofibric acid at 3.9 min. Insets in A and B represent the unique UV-Vis absorbance spectra of the obtained peaks corresponding to fenofibrate and fenofibric acid, respectively. D: Quantitative analysis of fenofibrate (FF) and fenofibric acid (FA) in membrane (M) and cytosolic (C) fractions isolated from LN-229 cells exposed to 50 µM fenofibrate (FF50) for 24 hrs. Concentrations of FF and FA were calculated from the corresponding calibration curves, and are expressed in µMs of FF and FA per $1 \times 10^6$ cells. Data represent average values from three separate measurements with standard deviation. Panel D: Western blot analysis demonstrating purity of cytosolic (C) and membrane (M) fractions in which N-Cadherin and GAPDH were use as membrane and cytosolic markers, respectively.

Anticancer effects of PPARα agonists, including fenofibrate, have been postulated by several laboratories. In addition, some anticancer effects of fenofibrate are suspected to be PPAR-independent. It has been also reported that fenofibrate may have cholesterol-like effects on biological membranes. Here we demonstrate, for the first time, the detection of fenofibrate in the membrane fraction isolated from human glioblastoma cells, LN-229 (FIG. 41). The cells were subjected to subcellular fractionation following the treatment with 25 µM fenofibrate (FF25) for 24 hrs. The results in FIG. 41A show HPLC analysis of the membrane fraction, which demonstrates a single peak at the retention time (RT)=10.4 min—almost identical to the RT of the fenofibrate standard (10.3 min; FIG. 39A). The membrane fraction isolated from control, DMSO-treated cells, was completely negative (data not shown). To further verify that the obtained peak corresponded to fenofibrate, the fraction was spiked with a 5 µl aliquot of fenofibrate (from 25 µM fenofibrate standard) just before HPLC separation. This procedure generated again a single peak that reflects quantitatively the sum of detected membrane fenofibrate and the fenofibrate spike (not shown). When cytosolic fraction was analyzed (FIG. 41B), it generated two distinct peaks: the first detected at RT=3.9 min, which corresponded to FA, and a second at RT=10.4 min, which corresponded to unprocessed FF. In addition, spectral analyses of the obtained peaks (insets in FIG. 41) matched with corresponding spectral analyses for FF and FA standards (FIG. 39A), further supporting their identity. The results in FIG. 41C show the quantitative analysis of FF and FA in cytosolic (cyto) and membrane (mem) fractions isolated from $1 \times 10^6$ LN-229 cells treated with 25 µM fenofibrate for 24 hrs. In membrane fractions, we detected 1.68 nmol of FF, but the levels of FA were below our limit of detection (that is approximately 0.1 µM for both FF and FA). Cytosolic fractions contained 2.40 nmol of FF and 0.57 nmol of FA per 10$^6$ cells. The purity of analyzed subcellular fractions was determined by Western blot analysis in which GAPDH served a cytosolic marker, and N-cadherin as a membrane marker, respectively (FIG. 41D). This novel finding indicates that unprocessed fenofibrate partitions into biological membranes, which in addition to the PPARα-mediated metabolic effect could contribute to the exceptional anticancer activity of this lipid-lowering drug.

FENOFIBRATE TISSUES DISTRIBUTION FOLLOWING ORAL ADMINISTRATION IN MICE. Considering possible anticancer application of fenofibrate, we decided to evaluate tissue distribution of FF and FA in mice after oral administration of 50 mg/kg/day of micronized fenofibrate. The results of the HPLC analysis are reported in the Table 1, below, which shows HPLC-based quantification of fenofibrate (FF) and fenofibric acid (FA) in different tissues and body fluids of mice fed with micronized fenofibrate (50 mg/kg/day) over a period of four weeks. The data are expressed as average values of FF and FA concentration (nmol/mg or nmol/ml) with standard deviation (n values range between 6 and 4), and were calculated using FF and FA calibration curves. For body fluids concentrations are calculated per ml of the body fluid, and in solid tissues per mg of the tissue.

TABLE 1

| Tissue (mg)/body fluid (ml) | FA (nmol/mg or /ml) | FF (nmol/mg or /ml) |
|---|---|---|
| Liver (n = 6) | 11.35 +/− 3.9 | 0 |
| Kidneys (n = 6) | 1.5 +/− 0.8 | 0 |
| Brain (n = 5) | 0.06 +/− 0.1 | 0 |
| Heart (n = 4) | 1.31 +/− 1.4 | 0 |
| Lungs (n = 6) | 0.36 +/− 04 | 0 |
| Spleen (n = 4) | 1.33 +/− 1.1 | 0 |
| Intracranial tumor (n = 6) | 0 | 0 |
| Blood (n = 6) | 3.33 +/− 1.6 | 0 |
| Urine (n = 5) | 5.34 +/− 2.4 | 0 |

Importantly, we did not detect FF in any of the analyzed tissues. The FA was detected in the blood plasma, urine, liver, kidneys, heart, spleen and lungs of the treated mice. In addition, we have detected very small amounts of FA in the intact brain tissue from two out of six mice treated with fenofibrate; however, LN-229 cells growing intracranially in these animals were completely negative. These data indicate that oral administration of FF is very unlikely to be successful in the treatment of intracranial tumors.

NEW EXPERIMENTAL STRATEGY FOR FENOFIBRATE DELIVERY TO THE TUMOR SITE. Since our previous studies demonstrated a very effective anticancer action of FF against brain tumor cells in vitro, and apparently FF and FA do not cross BBB or blood tumor barrier (BTB) efficiently enough to be detected by HPLC (Table 1), we needed to develop alternative approaches for the delivery of fenofibrate directly to the brain tumor site. Aggressive glial tumors are usually subjected to a surgical excision, which unfortunately does not guarantee recovery, and frequently patients experience tumor recurrence. Therefore, it is reasonable to propose a direct delivery of the drug into the cavity that is formed after tumor resection, in order to inhibit the glioblastoma cells that remain in the bed of the brain tissue. As a fenofibrate carrier, we employed a porous nanostructured poly-lactic-co-glycolic acid (PLGA) polymer matrix as shown in FIG. 38B. PLGA is a biodegradable, FDA approved polymer useful for both hydrophobic and hydrophilic drug delivery applications.

Figure 42:
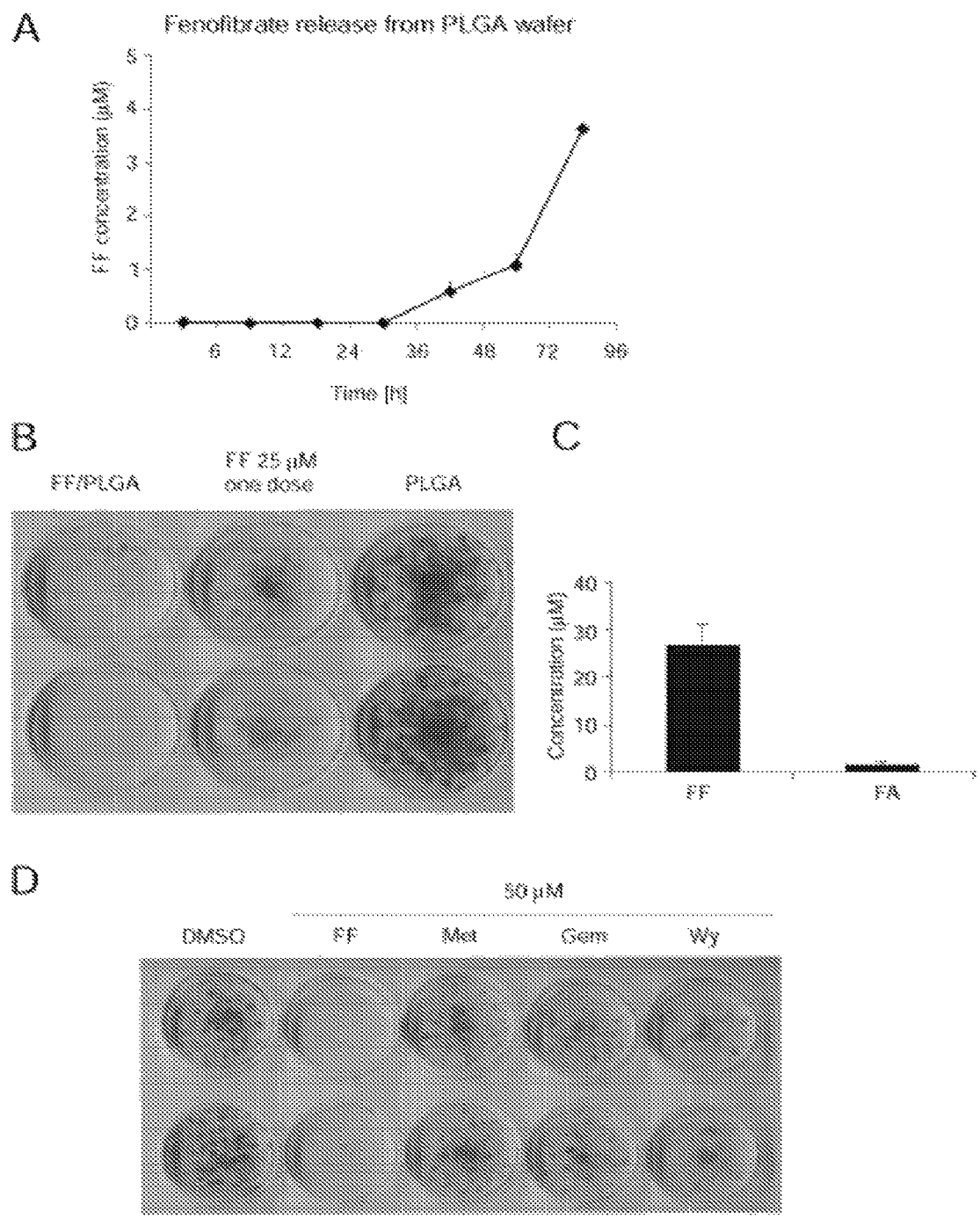
FIG. 42 is an illustration of an evaluation of the release of FF from a PGLA wafer produced according to the process illustrated in FIG. 40.

FIG. 42 illustrates an evaluation of PLGA wafer containing 1 mg of fenofibrate. Panel A: HPLC-based measurement of fenofibrate (FF) release to the culture media, after submerging the PLGA wafer containing 1 mg of fenofibrate. The analysis was performed in the absence of cells. Panel B: Clonogenic growth of LN-229 cells in the presence of PLGA wafer containing 1 mg of fenofibrate (PLGA/FF); empty wafer (PLGA); and fenofibrate in DMSO applied as a single 50 µM dose (FF50 µM). Panel C: Fenofibrate and fenofibric acid concentrations in LN-229 cells cultured in the presence of PLGA/FF wafer for 12 days. Panel D: Clonogenic assay in LN-229 cells treated with different PPARα agonists and Metformin: DMSO (vehicle), FF—fenofibrate 50 µM, Met—metformin 50 µM; Gem—gemfibrozil 50 µM, Wy—Wy14,643 50 µM. Cells were treated with the indicated compounds for 12 days; medium with the drugs was changed every third day. Data are expressed as average values with standard deviation (n=6).

The use of highly porous PLGA matrix with 1 mg of incorporated fenofibrate enabled slow release of the drug to the surrounding fluid with an increasing rate that is a consequence of drug diffusion and wafer erosion. The results in FIG. 42 show that fenofibrate-loaded PLGA matrix (PLGA/FF) submerged into the cell culture medium began to release FF after 36 hr, and the concentration of the drug constantly increased, reaching almost 4 µM after 4 days of the exposure. To determine whether the fenofibrate released from the PLGA matrix was still active against glioblastoma cells, we compared PLGA/FF with a single dose of 50 µM FF using the LN-229 clonogenic assay. The results in FIG. 6B demonstrated that the fenofibrate continuously released from the PLGA matrix inhibited clonal growth of LN-229 cell even more potently than a single dose of 50 µM fenofibrate. This could be attributed to a constant release of the active drug from the matrix, which seems to have an advantage over a single addition of FF. This is most likely because FF is quickly converted to FA, which has significantly lower anticancer activity in comparison to the unprocessed FF. The results in FIG. 42C show cumulative concentrations of FF and FA in culture media collected from the clonogenic assay, in which the PLGA/FF wafer was continuously present for 12 days. The data confirm the abundant presence of FF, which reached concentration of almost 30 µM at day 12 of the clonogenic assay. Conversely, we have detected only very low levels of FA in the same medium, which could be explained by a very low number of the tumor cells due to FF-induced inhibition of their clonogenic growth.

Since, FF-induced inhibition of glioblastoma clonogenic growth is indeed quite remarkable, we decided to compare fenofibrate with other known drugs that are postulated to have a similar anticancer activity, including other agonists of PPARα, gemfibrozil Wy-14,643, and an anti-diabetic drug metformin that is believed to induce energetic stress in cancer cells. The results in FIG. 42D show that FF is far more potent against LN-229 cells when directly compared to gemfibrozil, Wy-14,643, and metformin (all used at 50 µM, and with the addition of a fresh aliquot for each drug every third day). These results also suggests that PPARα-independent mechanism is a strong contributing factor in this FF-mediated inhibition of LN-229 cells, and that direct interaction between FF and cellular membranes (FIG. 41A) could be involved.

DISCUSSION. As previously reported, fenofibrate exerts strong antiproliferative, antimetastatic and proapoptotic activities towards various tumors of neuroectodermal origin, including glioblastoma, melanoma and medulloblastoma. This is a very interesting finding for a drug that originally was used for normalizing plasma lipid and lipoprotein profiles in patients with hypercholesterolemia. The potent anticancer activity of fenofibrate has gained much attention and has led to its incorporation within clinically applied drug regimens for patients with aggressive, recurrent brain malignancies, childhood primitive neuroectodermal tumors (PNETs) and leukemias. These regimens include COMBAT (Combined Oral Metronomic Biodifferentiating Antiangiogenic Treatment) and other metronomic antiangiogenic therapies. Metronomic chemotherapy is defined as chronic administration of chemotherapeutic and cytostatic drugs at relatively low doses to minimize toxicity and acute side effects. Importantly, this treatment scheme omits the drug-free recovery periods that usually lead to the tumor growth acceleration. Antiangiogenic multidrug metronomic regimens combining bevacizumab, thalidomide, celecoxib, etoposide, cyclophosphamide and fenofibrate or antiangiogenic differentiating regimen that include temozolomide, etoposide, celecoxib, vitamin D, fenofibrate and retinoic acid, are well tolerated and produce encouraging effects in pediatric patients with aggressive brain tumors. These benefits include increased 2-year survival, good overall response to the treatment and only minor side effects. Apart from being a treatment option for patients with brain malignancies, fenofibrate has been shown to exert neuroprotective effects in traumatic brain injuries and ischemic stroke. In animal models of ischemic stroke that involve temporal middle cerebral artery occlusion and subsequent reperfusion, mice pretreated with fenofibrate had significantly decreased cerebral infarct volume in the cortex and reduced oxidative stress in the brain tissue. These effects have been attributed to the antiinflammatory and antioxidative activity PPARα, because fenofibrate had no effect on ischemic/reperfussion injury in PPARα−/− mice. Of note, in this study the fenofibrate/fenofibric acid concentration in the brain was not actually measured. To assess fenofibrate penetration to brain tissue, the authors employed a blood-brain barrier (BBB) in vitro model that consisted of bovine capillary endothelial cells and rat astrocytes cocultured in the cell culture vessels with inserts. The estimated BBB permeability coefficient for fenofibric acid was very low ($0.68 \times 10^{-3}$ cm/min) and similar to that of sucrose, so the authors concluded that this molecule crosses BBB at a very slow rate. Therefore, we might assume that the FA concentration in the brain might teeter on the edge of detection limit of HPLC method, as was present in this study. Another interesting study that recognized a neuroprotective potential of fenofibrate tried to address the problem of poor access to the brain tissue through BBB by developing fenofibrate and fenofibric acid loaded PLGA microparticles for intracranial delivery. The drug-containing microparticles were injected intracranially to rats prior to the stroke induction. That procedure allowed the injection of 10 µl of the suspension, which due to the relatively low drug release rate (estimated not to exceed 0.004% daily,) limited the drug accessibility area. It is remarkable that in this study, fenofibrate, in contrast to fenofibric acid, significantly reduced cortical infarct volume, despite its much lower solubility. In the light of our results, this might be attributed to better solubility of fenofibrate in the neuronal plasma membranes. It cannot be excluded that the neuroprotective activity of fenofibrate and the lack of such for fenofibric acid could be associated with the PPARα independent, direct interactions with biological membranes. The study by Gamerdinger and colleagues (Gamerdinger M, Clement A B, Behl C. Cholesterol-Like Effects of Selective Cyclooxygenase Inhibitors and Fibrates on Cellular Membranes and Amyloid—Production □. Mol Pharmacol 2007; 72:141-51.) presented the evidence that fenofibrate influenced the membrane fluidity in the manner similar to cholesterol, and particularly increased the long fatty acid chain order that resulted in a thicker and more rigid membrane. We believe that the strong anti-proliferative and anti-invasive effects of fenofibrate against glioblastoma cells are largely PPARα independent, because other specific PPARα agonists, such as Wy-14,643 or Gemfibrozil are not able to reproduce them (FIG. 44D), and PPARα siRNA mediated silencing does not abolish them completely. This notion can be further supported by the results showing the fenofibrate accumulation in the cellular membranes, where it is neither converted into the PPARα ligand, fenofibric acid, nor interacts with the receptor.

Numerous independent reports indicate that membrane lipid composition and biophysical properties differ between brain tumors and healthy brain tissue. Most reports describe a decreased phosphatidylethanoloamine and phosphatidylserine content, reduced n-3 polyunsaturated fatty acid (DHA) and increased n-6 linoleic acid levels in brain metastatic tumors, meningiomas and gliomas in comparison to white and grey matter. Despite these observations, unequivocal correlation between invasiveness or high metastatic potential and membrane fluidity have not been confirmed. Nevertheless, interesting effects of nonsteroid anti-inflammatory drugs (NSAIDs: aspirin, celecoxib, etoricoxib) were noted in membrane dynamics during chemically induced colon carcinogenesis in rats. Progressive carcinogenesis was associated with decline in cholesterol content and reduced cholesterol to phospholipid ratio in the cell membranes. Alterations in lipid composition resulted in more fluid and less ordered membrane structure. NSAIDs mimicked cholesterol effects and restored membrane polarization and lipid order in membranes such that they resembled membranes in healthy tissue, thus leading to chemoprevention. It is possible that fenofibrate accumulation in the membranes induces similar effects. In conclusion, it is possible that membrane directed, PPARα-independent actions of fenofibrate could have a contribution equal to or even more important than its PPARα-mediated effects in drug therapy for glioblastoma patients after tumor resection.

In this study we present the rationales for future clinical trials with the fenofibrate-loaded PLGA matrices (wafers) to be placed intracranially in the cavity that remains after glioma resection. This approach, together with standard chemotherapy or metronomic treatment, could limit the danger of recurrence and lead to substantial improvement in the prognosis for the patients. PLGA is both biocompatible with brain tissue and biodegradable, which means that the drug release is driven by both diffusion through the polymer and erosion (hydrolysis) of the carrier. Both diffusion and erosion require a liquid environment, which is present in the tumor resection area. Such PLGA-based systems have already been tested for carmustine, temozolomide and paclitaxel delivery for glioma treatment. One of PLGA's advantages is its relatively high hydrophobicity, which enables efficient encapsulation of nonpolar drugs such as fenofibrate. Slow release of drug from the hydrophobic PLGA matrix might also favor drug distribution into the lipid rich neuronal tissue.

A number of embodiments have been described. Nevertheless it will be understood that various modifications may be made without departing from the spirit and scope of the invention. Accordingly, other embodiments are included as part of the invention and may be encompassed by the attached claims. Furthermore, the foregoing description of various embodiments does not necessarily imply exclusion. For example, a person of skill in the art reading this disclosure can readily understand that the concepts provided herein may be easily extended, for example to additional design elements of coatings on biological implants. As an example, the disclosure provides layered structures with PGLA films made using a breath figure technique, which films may facilitate multiple combinations of fast and slow release with multiple drug species as wells as the use of drug-free layers as sealants to control initial burst levels. In other words, for example, although the disclosure includes an example of treating brain cancer by incorporating fenofibrate into a PGLA polymer using the breath figure concept, other brain cancer therapeutic agents may be incorporated instead of or in addition to Fenofibrate. The specific example demonstrates the suitability of the drug delivery device approach presented herein but for example is not limited to the specific therapeutic agent. Similarly the use of the drug delivery device for treatment of brain cancer is a specific but not limiting example. The device may be understood more broadly to release drugs on contact with liquid and so may be used to treat other cancers such as bladder cancers. Thus too, "some" embodiments, "exemplary" embodiments, or "other" embodiments may include all or part of "some," "other," and "further" embodiments within the scope of this invention. In addition not all embodiments include one or more of the listed objects.

Example of Additional Embodiments

1. A therapeutic film comprising:
   a biodegradable polymer film; and
   a therapeutic drug.
2. The therapeutic film of embodiment 1 wherein the biodegradable polymer film comprises at least one of the following: gelatin; PLGA porous coating; PLGA/PEG composite porous coating; nonporous PLGA coating; nonporous PLGA/PEG composite coating.
3. The therapeutic film of embodiment 2 wherein the biodegradable polymer film comprises a PLGA coating.
4. The therapeutic film of embodiment 1 wherein the biodegradable polymer film is made using a breath figure technique.
5. The therapeutic film of embodiment 4 further comprising a second biodegradable polymer film.
6. The therapeutic film of embodiment 5 further comprising a second therapeutic drug.
7. The therapeutic film of embodiment 6 wherein the first therapeutic drug is dispersed within the biodegradable polymer film and the second therapeutic drug is loaded into pores on the biodegradable polymer film.
8. The therapeutic film of embodiment 7 further comprising a glaucoma drainage device to which the therapeutic film is attached.
9. The therapeutic film of embodiment 8 wherein the therapeutic film is attached to the glaucoma drainage device by a PLGA string.
10. The therapeutic film of embodiment 8 wherein the therapeutic film is attached to the glaucoma drainage device by glue.
11. The therapeutic film of embodiment 7 wherein at least one of the therapeutic drugs is mytomycin C.
12. The therapeutic film of embodiment 7 wherein at least one of the therapeutic drugs is 5-fluorouracil.
13. The therapeutic film of embodiment 7 wherein at least one of the therapeutic drugs is a treatment for cancer.
14. A method of preparing a therapeutic film comprising:
    Dissolving a therapeutic drug in the aqueous part of a water in oil emulsion;
    Dissolving a biodegradable polymer in dichloromethane; and
    Spin coating the emulsion and the polymer solution in a humid environment.
15. The method of embodiment 14 wherein the biodegradable polymer film comprises at least one of the following: gelatin; PLGA porous coating; PLGA/PEG composite porous coating; nonporous PLGA coating; nonporous PLGA/PEG composite coating.
16. The method of embodiment 15 wherein the biodegradable polymer film comprises a PLGA coating.
17. The method of embodiment 14 further comprising a casting a second biodegradable polymer film on top of the first biodegradable polymer film.
18. The method of embodiment 17 further comprising loading a second therapeutic drug into the pores of a biodegradable polymer film.
19. The method of embodiment 14 further comprising attaching the therapeutic film to a glaucoma drainage device.
20. The method of embodiment 19 wherein the therapeutic film is attached to the glaucoma drainage device by a PLGA string.
21. The method of embodiment 20 wherein the therapeutic film is attached to the glaucoma drainage device by glue.
22. The method of embodiment 17 further comprising implanting the therapeutic film into a patient with cancer.
23. A layered device for drug delivery, comprising:
    at least one polymeric film layer made by a breath figure technique; and
    at least one therapeutic agent.
24. A layered device according to embodiment 23, wherein the at least one polymeric film layer is a first polymeric film layer and a second polymeric film layer, and the at least one therapeutic agent is a first therapeutic agent associated with the first polymeric film layer.
25. A layered device according to embodiment 23, wherein the device is made by a process comprising spin coating a mixture comprising a first polymer and the therapeutic agent onto a substrate to produce the first layer, and spin coating a second polymer onto the first layer to produce the second layer, and further wherein the first polymer and the second polymer can be the same polymer.
26. A layered device according to embodiment 22, wherein the at least one polymeric film layer is a first polymeric film layer and a second polymeric film layer, and the at least one therapeutic agent is a first therapeutic agent associated with the first polymeric film layer and a second therapeutic agent associated with the second layer, wherein the first therapeutic agent and the second therapeutic agent can be the same therapeutic agent.
27. A layered device according to embodiment 25, wherein the first therapeutic drug is dispersed within the first polymeric film layer and the second therapeutic drug is loaded into pores of the second polymeric film layer.
28. A layered device according to embodiment 26, wherein the device is made by a process comprising spin coating a mixture comprising a first polymer and a first therapeutic agent onto a substrate to produce the first layer, spin coating a second polymer onto the first layer to produce the second layer, and injecting a second therapeutic agent into the pores of the second polymer layer after producing the second polymer layer; and further wherein the first polymer and the second polymer can be the same polymer.
29. A layered device according to embodiment any of embodiments 22-27, wherein the at least one polymeric layer comprises a biodegradable polymer and optionally comprises a pore-forming agent.
30. A layered device according to embodiment 28, wherein at least one of the at least one polymeric layers comprises a biodegradable polymer and a pore-forming agent.
31. A layered device according to embodiments 28 or 29, wherein the biodegradable polymer is a PLGA and the pore-forming agent is PEG.
32. A layered device according to embodiment 30, wherein the ratio of PEG to PLGA was 1:9.
33. A device according to any of embodiments 22-31, further comprising a glaucoma drainage device to which the layered device is attached.
34. A device according to embodiment 32, wherein the layered device is attached to the glaucoma drainage device by a PLGA string.
35. A device according to claim 32, wherein the layered device is attached to the glaucoma drainage device by glue.
36. A device according to embodiment 32, wherein the layered device is coated onto the glaucoma drainage device.
37. A device according to any of embodiments 22-35, wherein the at least one therapeutic agent is chosen from mytomycin C, 5-fluorouracil and combinations thereof.
38. A device according to any of embodiments 22-27, wherein at least one therapeutic drug is chosen from anticancer agents.
39. A device according to embodiment 37, wherein the at least one therapeutic drug is Fenofibrate.
40. A method of preparing a therapeutic film comprising: producing a film comprising a therapeutic agent by a breath figure technique.
41. A method according to embodiment 39, wherein the method comprises:
  dissolving a therapeutic drug in an aqueous portion of a water in oil emulsion;
  dissolving a biodegradable polymer in a solvent; and
  spin coating the emulsion and the polymer solution in a humid environment to form a first biodegradable polymer film.
42. A method according to embodiment 39 or 40, wherein the film (for example wherein the biodegradable polymer) comprises PG LA.
43. A method according to any of embodiments 39-41, wherein the film comprises a polymer and a pore-forming agent (for example wherein dissolving a biodegradable polymer comprises dissolving a biodegradable polymer and a pore-forming agent in a solvent).
44. A method according to embodiment 42, wherein the polymer is a PLGA and the pore-forming agent is PEG.
45. A method according to any of embodiments 39-43, further comprising casting a second biodegradable polymer film on top of the first biodegradable polymer film.
46. A method according to embodiment 44, further comprising loading a second therapeutic drug into the second biodegradable polymer film by spin coating the drug with the polymer or by injecting the drug into the pores of the already-produced second biodegradable polymer film.
47. A method of treating glaucoma, comprising implanting a glaucoma drainage device associated with a layered device according to any of embodiments 22-35 in a subconjunctival space of a patient.
48. A method of treating glaucoma, comprising implanting a glaucoma drainage device associated with a layered device according to embodiment 22, wherein the layered device comprises a first polymeric layer associated with a first therapeutic drug and a second polymeric layer associated with a second therapeutic drug, wherein the first therapeutic drug is 5-Fu and the second therapeutic drug is MMC.
49. A method according to embodiment 45, wherein the layered device is made by the process of spin coating a mixture of an emulsion comprising the first therapeutic drug and a polymer solution onto a substrate to produce a first polymeric film layer, spin coating a second polymer solution onto the first polymeric film layer to produce a porous second polymeric film layer and loading the pores of the second polymeric film layer with the second therapeutic drug.
50. A method according to any of embodiments 46-48, wherein the layered device is configured to result in at least a burst release of first therapeutic drug (for example MMC) and at least a slow release of second therapeutic drug (e.g. 5-FU).
51. A method of treating cancer, comprising implanting a layered device according to embodiment 22 in a patient in need of cancer therapy, wherein the at least first therapeutic agent is an anticancer agent.
52. A method of treating cancer according to embodiment 40, wherein implanting comprises implanting the layered device at the site of a brain tumor and the anticancer agent is Fenofibrate.
53. A method of treating cancer according to embodiment 51, wherein the layered device is a first polymeric layer formed from PGLA in the form of a wafer loaded with Fenofibrate.
54. A method of preparing a therapeutic film comprising: spin coating a first therapeutic agent with a polymer solution in a humid environment.
55. A method according to embodiment 54 wherein the first therapeutic agent is dissolved in the aqueous part of a water in oil emulsion; and the method further involves dissolving a biodegradable polymer in dichloromethane to form the polymer solution; and spin coating involves spin coating the emulsion and the polymer solution in a humid environment.
56. A method according to embodiment 54 wherein fine particles of the first therapeutic agent are dispersed or dissolved, as appropriate, in the polymer solution (for example a polymer solution made by dissolving a biodegradable polymer in dichloromethane) prior to spin coating the therapeutic agent with the polymer solution.
57. A drug delivery device, comprising:
  a therapeutic film comprising one or more layers of polymeric film made by a breath figure technique; and, a therapeutic agent.
58. A drug delivery device according to embodiment 57 wherein the therapeutic film comprises a first polymeric film layer associated with a first therapeutic agent.

59. A drug delivery device according to embodiment 58, wherein the therapeutic film further comprises a second polymeric film layer.
60. A drug delivery device according to embodiment 58, wherein the first therapeutic agent is dispersed within the first polymeric layer.
61. A drug delivery device according to embodiment 60, wherein the therapeutic film is made by a process comprising spin coating a mixture comprising a first polymer solution and an emulsion containing the first therapeutic agent onto a substrate to produce the first polymeric layer.
62. A drug delivery device according to embodiment 58, wherein the first therapeutic agent is loaded into pores of the first polymeric layer.
63. A drug delivery device according to embodiment 63, wherein the first therapeutic agent is injected into the pores of the first polymeric layer after the first polymer layer is made.
64. A drug delivery device according to embodiment 59, wherein the therapeutic film further comprises a second therapeutic agent and the first therapeutic agent is dispersed into the first polymeric film and the second therapeutic agent is loaded into pores of the second polymer film.
65. A drug delivery device according to embodiment 64, wherein the second polymeric film layer is spun coated onto the first polymer film layer.
66. A drug delivery device according to embodiment 57, wherein the one or more polymeric layers comprise a biodegradable polymer and optionally comprise a pore-forming agent.
67. A drug delivery device according to embodiment 58, wherein the first polymeric layer comprises biodegradable polymer chosen from a PLGA and the first polymeric layer also comprises a pore-forming agent chosen from PEGs.
68. A drug delivery device according to embodiment 67, wherein the PLGA and the PEG are present in the first polymeric film layer in a ratio of about 1:9.
69. A drug delivery device according to embodiment 57, further comprising a glaucoma drainage device attached to the therapeutic film.
70. A drug delivery device according to embodiment 69, wherein the therapeutic film is attached to the glaucoma drainage device by a PLGA string.
71. A drug device according to embodiment 69, wherein the therapeutic film is attached to the glaucoma drainage device by glue.
72. A drug delivery device according to embodiment 69, wherein the therapeutic film is coated onto the glaucoma drainage device.
73. A drug delivery device according to embodiment 64, further comprising a glaucoma drainage device attached to the therapeutic film, and further wherein the first therapeutic agent is 5-fluoruoracil and the second therapeutic agent is mytomycin C.
74. A drug delivery device according to embodiment 58 wherein the first therapeutic agent is chosen from anticancer agents.
75. A drug delivery device according to embodiment 74, wherein the anticancer agent is Fenofibrate.
76. A method of making a drug delivery device comprising: producing a polymeric film layer comprising a therapeutic agent using a breath figure technique.
77. A method according to embodiment 76, wherein producing the polymer film layer comprises:
dissolving a biodegradable polymer in a solvent; and spin coating the polymer solution along with a therapeutic drug in a humid environment to form a first biodegradable polymeric film layer.
78. A method according to embodiment 77, wherein the biodegradable polymer comprises PG LA.
79. A method according to embodiment 78, further comprising dissolving PEG in the solvent with the biodegradable polymer.
80. A method according to embodiment 77, further comprising casting a second biodegradable polymeric film layer on top of the first biodegradable polymeric film layer.
81. A method according to embodiment 80, further comprising loading a second therapeutic drug into pores of the second biodegradable polymeric film layer.
82. A method of treating glaucoma, comprising implanting a glaucoma drainage tube according to embodiment 69 in a subconjunctival space of a patient.
83. A method according to embodiment 69 wherein the therapeutic film comprises a first polymeric layer associated with a first therapeutic drug and a second polymeric layer associated with a second therapeutic drug, and the first therapeutic drug is 5-Fu and the second therapeutic drug is MMC.
84. A method according to embodiment 83, wherein the layered device is configured to result in at least a burst release of MMC and at least a slow release of 5-FU.
85. A method of treating cancer, comprising implanting a drug delivery device according to embodiment 74 in a patient in need of cancer therapy.
86. A method of treating cancer according to embodiment 85, wherein implanting comprises implanting the drug delivery device at the site of a brain tumor and the anticancer agent is Fenofibrate.
87. A method of treating cancer according to embodiment 86, wherein the drug delivery device is a therapeutic film comprising a first polymeric layer formed from PGLA in the form of a wafer loaded with Fenofibrate.
88. A method according to embodiment 77, further comprising dissolving the therapeutic drug in an aqueous portion of a water-in-oil emulsion, and wherein spin coating the polymer solution along with the therapeutic drug comprises spin coating the emulsion and the polymer solution.
89. A method according to embodiment 77, wherein spin coating the polymer solution along with the therapeutic drug comprises dispersing or dissolving the therapeutic drug into the polymer solution prior to spin coating.

What is claimed is:

1. A drug delivery device, consisting of a multi-layer film, wherein the multi-layer film comprises at least a first layer comprising a first anti-fibrotic drug associated with a first biodegradable polymer film; and, at least a second layer comprising a second anti-fibrotic drug associated with a second biodegradable polymer film, wherein the first layer of the drug delivery system is configured to provide a sustained release of the first anti-fibrotic drug and the second layer of the drug delivery system is configured to provide a burst release of the second anti-fibrotic drug on contact with the aqueous humor, where the first biodegradable polymer film and the second biodegradable polymer film comprise a poly lactic-co-glycolic acid ("PLGA"), and at least the first biodegradable polymer film further comprises a polyethyleneglycol ("PEG") in a ratio of about 1:9 of PLGA:PEG.

2. A drug delivery device according to claim 1, wherein the first anti-fibrotic drug is 5-flurouracil ("5-FU") and the second anti-fibrotic drug is mitomycin C ("MMC").

3. A drug delivery device according to claim 2, wherein the 5-FU is released over a period of at least 30 days, and the MMC is released in a period of about 24 hours.

4. A drug delivery device according to claim 3, wherein sustained release of the 5-FU begins after about 24 hours.

5. A drug delivery device according to claim 4, wherein sustained release of the 5-FU begins after about 3-5 days.

6. A drug delivery device according to claim 1, wherein the first biodegradable polymer film and the second biodegradable polymer film degrade within about 3 months after contact with aqueous humor.

7. A drug delivery device according to claim 1, wherein the first biodegradable polymer film and the second biodegradable polymer film degrade in from about 30-60 days.

8. A drug delivery device according to claim 1, wherein the first biodegradable polymer film and the second biodegradable polymer film are made using a breath figure technique.

9. A drug delivery device according to claim 1, wherein the first anti-fibrotic drug is dispersed within the first polymeric film.

10. A drug delivery device according to claim 1, wherein the first layer is made by a process comprising spin coating the first anti-fibrotic drug with a polymer solution comprising the first biodegradable polymer, the second polymeric film is spin coated onto the first layer, and the second therapeutic agent is a second anti-fibrotic drug which is loaded into pores of the second polymeric film after the second polymeric film is made.

11. A drug delivery device according to claim according to claim 10, wherein: the first anti-fibrotic drug is 5-FU; the second anti-fibrotic drug is MMC; the multi-layer film is a dual-layer film; and, the first layer is formed by spin-coating 5-FU dissolved into a PLGA solution and the second layer is formed by loading MMC into the pores of an already-prepared second biodegradable PLGA film.

12. A drug delivery device according to claim 1, wherein upon contact with the aqueous humor during glaucoma surgery, the first layer of the drug decreases fibroblast activity for up to about four weeks, and the second layer of the drug decreases immediate post-operative wound healing response.

13. A method of making the drug delivery device according to claim 1, comprising dissolving the first biodegradable polymer in a solvent to form a polymer solution, and spin coating the polymer solution along with the first anti-fibrotic drug in a humid environment to form the first layer; casting the second biodegradable polymer on top of the first layer to form the second layer; and, loading the second anti-fibrotic drug into pores of the second layer wherein the first biodegradable polymer comprises PLGA and PEG in a ratio of about 1:9 and the second biodegradable polymer comprises a PLGA.

14. A method of treating glaucoma, comprising implanting a drug delivery device according to claim 1 in a subconjunctival space of a patient.

15. A method according to claim 14, wherein the first anti-fibrotic drug is 5-FU and the second therapeutic drug is MMC.

* * * * *